United States Patent
Scott et al.

(10) Patent No.: US 11,737,978 B2
(45) Date of Patent: Aug. 29, 2023

(54) COMPOSITIONS AND METHODS OF USING PROPYLENE SULFIDE-BASED POLYMERS FOR TREATMENT OF CHAGAS DISEASE

(71) Applicant: Northwestern University, Evanston, IL (US)

(72) Inventors: Evan A. Scott, Evanston, IL (US); Sijia Yi, Evanston, IL (US); David Engman, Evanston, IL (US); Xiaomo Li, Evanston, IL (US)

(73) Assignee: Northwestern University, Evanston, IL (US)

( * ) Notice: Subject to any disclaimer, the term of this patent is extended or adjusted under 35 U.S.C. 154(b) by 232 days.

(21) Appl. No.: 16/942,267

(22) Filed: Jul. 29, 2020

(65) Prior Publication Data

US 2021/0052498 A1     Feb. 25, 2021

Related U.S. Application Data

(60) Provisional application No. 62/880,013, filed on Jul. 29, 2019.

(51) Int. Cl.
| | | |
|---|---|---|
| *A61K 9/127* | (2006.01) | |
| *A61K 31/4168* | (2006.01) | |
| *A61P 33/02* | (2006.01) | |
| *A61K 47/34* | (2017.01) | |
| *A61K 9/107* | (2006.01) | |

(52) U.S. Cl.
CPC .......... *A61K 9/1273* (2013.01); *A61K 9/1075* (2013.01); *A61K 31/4168* (2013.01); *A61K 47/34* (2013.01); *A61P 33/02* (2018.01)

(58) Field of Classification Search
CPC .. A61K 31/4168; A61K 47/34; A61K 9/1075; A61K 9/1273; A61K 9/514; A61P 33/02; Y02A 50/30
See application file for complete search history.

(56) References Cited

U.S. PATENT DOCUMENTS 10,633,493 B2     4/2020    Scott

OTHER PUBLICATIONS

Allen, S. et al. "On the advancement of polymeric bicontinuous nanospheres toward biomedical applications." Nanoscale Horizons 4.2 (2019): 258-272.
Allen, S. et al. "Rapid, scalable assembly and loading of bioactive proteins and immunostimulants into diverse synthetic nanocarriers via flash nanoprecipitation." JoVE (Journal of Visualized Experiments) 138 (2018): e57793.
Allen, S. et al. (2016). Engineering nanomaterials to address cell-mediated inflammation in atherosclerosis. Regenerative engineering and translational medicine, 2(1), 37-50.
Allen, S. et al. Benchmarking bicontinuous nanospheres against polymersomes for in vivo biodistribution and dual intracellular delivery of lipophilic and water soluble payloads . . . ACS Appl. Mater. Interfaces 2018, 10, 40, 33857-33866.
Allen, S. et al. Celastrol-loaded PEG-b-PPS nanocarriers as an anti-inflammatory treatment for atherosclerosis. Biomater Sci. 2019;7:657-68.

(Continued)

*Primary Examiner* — Savitha M Rao
(74) *Attorney, Agent, or Firm* — Quarles & Brady LLP

(57) ABSTRACT

The present invention provides novel nanostructures comprising solution of $PPSU_{20}$. Methods of preparing the novel PPSU nanostructures, and applications of such nanostructures are also provided.

15 Claims, 8 Drawing Sheets
(7 of 8 Drawing Sheet(s) Filed in Color)

Specification includes a Sequence Listing.

(56) References Cited

OTHER PUBLICATIONS

Allen, S. et al. Facile assembly and loading of theranostic polymersomes via multi-impingement flash nanoprecipitation. J Control Release. 2017;262:91-103.

Allen, S. et al. Polymersomes scalably fabricated via flash nanoprecipitation are non-toxic in non-human primates and associate with leukocytes in the spleen and kidney following intravenous administration. Nano Res. 2018;11:5689-703.

Andrade DV, et al. Acute chagas disease: new global challenges for an old neglected disease. PLoS Negl Trap Dis. 2014;8:e3010.

Andrews NW, et al. A T. cruzi-secreted protein immunologically related to the complement component C9: evidence for membrane pore-forming activity at low pH. Cell. 1990;61:1277-87.

Andrews NW, et al. Phagolysosomal escape by intracellular pathogens. Parasitol Today (Personal ed). 1991;7:335-40.

Apt, W. "Treatment of Chagas disease." American Trypanosomiasis Chagas disease. Elsevier, 2017. 751-771.

Arrua EC, et al. Nanocarriers for effective delivery of benznidazole and nifurtimox in the treatment of chagas disease: A review. Acta Tropica. 2019; 198:105080-.

Barenholz, Y. C. (2012). Doxil—the first FDA-approved nano-drug: lessons learned. Journal of controlled release, 160(2), 117-134.

Bern C. Antitrypanosomal Therapy for Chronic Chagas' Disease. N Engl J Med. 2011;364:2527-34.

Bobbala S, et al. Flash nanoprecipitation permits versatile assembly and loading of polymeric bicontinuous cubic nanospheres. Nanoscale. 2018;10:5078-88.

Bonney KM et al. Autoimmune pathogenesis of Chagas heart disease: looking back, looking ahead. The American journal of pathology. 2015;185:1537-47.

Bonney KM et al. Pathology and Pathogenesis of Chagas Heart Disease. Annu Rev Pathol. 2019;14:421-47.

Brannigan, R. P., et al. "Biomaterials Science aliphatic polyesters and polycarbonates Hydrolytic degradation." Biomater. Sci 5 (2017): 9-21.

Castro JA, et al. Toxic side effects of drugs used to treat Chagas' disease (*American trypanosomiasis*). Hum Exp Toxicol. 2006;25:471-9.

Castro-Sesquen YE, et al. Use of a Chagas Urine Nanoparticle Test (Chunap) to Correlate with Parasitemia Levels in T. cruzi/HIV Co-infected Patients. PLoS Negl Trop Dis. 2016;10:e0004407.

Cencig S, et al. Parasitic Loads in Tissues of Mice Infected with Trypanosoma cruzi and Treated with AmBisome. PLOS Negl Trap Dis. 2011;5:e1216.

Cevey AC, et al. Low-dose benznidazole treatment results in parasite clearance and attenuates heart inflammatory reaction in an experimental model of infection with a highly virulent Trypanosoma cruzi strain. Int J Parasitol Drugs Drug Resist. 2016;6:12-22.

Chagas C. Nova entidade morbida do homem: rezumo geral de estudos etiolojicos e clinicos. Mem Inst Oswaldo Cruz. 1911;3:219-75.

Chagas C. Nova tripanozomiaze humana: estudos sobre a morfolojia e o ciclo evolutive do *Schizotrypanum cruzi* n. gen., n. sp., ajente etiolojico de nova entidade morbida do homem. Mem Inst Oswaldo Cruz. 1909;1:159-218. With English Abstract.

Chatelain E. Chagas disease drug discovery: toward a new era. Journal of biomolecular screening. 2015;20:22-35.

Clayton J. Chagas disease 101. Nature. 2010;465:S4-S5.

Clemons KV, et al. Lack of Efficacy of Liposomal Amphotericin B Against Acute and Chronic Trypanosoma cruzi Infection in Mice. Am J Trap Med Hyg. 2017;97:1141-6.

Cooper DL, et al. Nanoparticles in drug delivery: mechanism of action, formulation and clinical application towards reduction in drug-associated nephrotoxicity. Expert Opin Drug Deliv. 2014;11:1661-80.

Coura Jr, et al. A Critical Review on Chagas Disease Chemotherapy. Memórias do Institute Oswaldo Cruz. 2002;97:3-24.

Coura Jr, et al. Chagas disease: a new worldwide challenge. Nature. 2010;465:S6-S7.

De Souza W, et al. Review on Trypanosoma cruzi: host cell interaction. Int J Cell Biol. 2010;2010.

DNDI. Study shows dramatically shorter treatment for Chagas disease could be just as effective, and significantly safer. Drugs for Neglected Diseases Initiative Web Site. https://dndi.org/press-releases/2019/study-shows-dramatically-shorter-treatment-chagas-effective-and-safer/. Published Mar. 14, 2019. Accessed Aug. 21, 2020.

Dowling DJ, et al. Toll-like receptor 8 agonist nanoparticles mimic immunomodulating effects of the live BCG vaccine and enhance neonatal innate and adaptive immune responses. J Allergy Clin Immunol. 2017;140:1339-50.

Du F. et al., Sequential intracellular release of water-soluble cargos from Shell-crosslinked polymersomes. J Control Release. 2018; 282:90-100.

Du, F., et al. "Immunotheranostic polymersomes modularly assembled from tetrablock and diblock copolymers with oxidation-responsive fluorescence." Cellular and molecular bioengineering 10.5 (2017): 357-370.

Du, F., et al., (2019): Homopolymer Self-Assembly via Poly(propylene Sulfone) Networks. ChemRxiv. Preprint.

Dvir, T., et al. "Nanotechnological strategies for engineering complex tissues." Nature nanotechnology 6.1 (2011): 13.

Dvir, T., et al. "Nanowired three-dimensional cardiac patches." Nature nanotechnology 6.11 (2011): 720-725.

Ezrahi S, et al. Basic principles of drug delivery systems—the case of paclitaxel. Adv Colloid Interface Sci. 2019;263:95-130.

Field MC, et al. Anti-trypanosomatid drug discovery: an ongoing challenge and a continuing need. Nat Rev Microbiol. 2017;15:217-31.

Garza M, et al. Projected future distributions of vectors of Trypanosoma cruzi in North America under climate change scenarios. PLoS Negl Trap Dis. 2014;8:e2818.

Gil-Jaramillo N, et al. Dendritic Cells: A Double-Edged Sword in Immune Responses during Chagas Disease. Front Microbiol. 2016;7:1076.

Goldberg DE, et al. Hardly Vacuous: The Parasitophorous Vacuolar Membrane of Malaria Parasites. Trends Parasitol. 2020;36:138-46.

Han, J., et al. "A simple confined impingement jets mixer for flash nanoprecipitation." Journal of pharmaceutical sciences 101.10 (2012): 4018-4023.

Krabin, N. B., et al. "Sustained micellar delivery via inducible transitions in nanostructure morphology." Nature communications 9.1 (2018): 1-13.

Kreuter J. Nanoparticles—a historical perspective. Int J Pharm. 2007;331:1-10.

Ladaviere C, et al. Toward an optimized treatment of intracellular bacterial infections: input of nanoparticulate drug delivery systems. Nanomedicine. 2015;10:3033-55.

Leiriao P, et al. Survival of protozoan intracellular parasites in host cells. EMBO Rep. 2004;5:1142-7.

Lewinsohn R. Carlos Chagas and the Discovery of Chagas's Disease (*American trypanosomiasis*). Journal of the Royal Society of Medicine. 1981.

Liu Q, et al. Preventing the transmission of American trypanosomiasis and its spread into non-endemic countries. Infect Dis Poverty. 2015;4:60.

Lopez M, et al. Pathogenesis of Chronic Chagas Disease: Macrophages, Mitochondria, and Oxidative Stress. Current Clinical Microbiology Reports. 2018;5:45-54.

Mazzeti AL, et al. Benznidazole self-emulsifying delivery system: A novel alternative dosage form for Chagas disease treatment. Eur J Pharm Sci. 2020;145:105234.

Miller, I. V., et al. "Tumour-derived exosomes: Tiny envelopes for big stories." Biology of the Cell 107.9 (2015): 287-305.

Molina I, et al. Randomized Trial of Posaconazole and Benznidazole for Chronic Chagas' Disease. N Engl J Med. 2014;370:1899-908.

Moncayo Á. Carlos Chagas: Biographical sketch. Acta Tropica. 2010;115:1-4.

Morelli, A. E., et al. "Tolerogenic dendritic cells and the quest for transplant tolerance." Nature Reviews Immunology 7.8 (2007): 610-621.

(56) References Cited

OTHER PUBLICATIONS

Morilla MJ, et al. Nanomedicines against Chagas disease: an update on therapeutics, prophylaxis and diagnosis. Nanomedicine (London, England). 2015;10:465-81.
Morillo CA, et al. Randomized trial of benznidazole for chronic Chagas' cardiomyopathy. N Engl J Med. 2015;373:1295-306.
Morrot A, et al. Evasion and Immuno-Endocrine Regulation in Parasite Infection: Two Sides of the Same Coin in Chagas Disease? Frontiers in Microbiology. 2016;7:704.
Napoli A, et al. Oxidation-responsive polymeric vesicles. Nat Mater. 2004;3:183-9.
Olivera MJ, et al. Risk factors for treatment interruption and severe adverse effects to benznidazole in adult patients with Chagas disease. PLOS ONE. 2017;12:e0185033.
Park, S.-H., et al. "CD 1-restricted T-cell responses and microbial infection." Nature 406.6797 (2000): 788-792.
Pastuzyn, E. D., et al. "The neuronal gene Arc encodes a repurposed retrotransposon Gag protein that mediates intercellular RNA transfer." Cell 172.1-2 (2018): 275-288.
Pérez-Molina JA, et al. Chagas disease. The Lancet. 2018;391:82-94.
Perin L, et al. Pharmacokinetics and Tissue Distribution of Benznidazole after Oral Administration in Mice. Antimicrob Agents Chemother. 2017;61:e02410-16.
Pinazo M-J, et al. Tolerance of Benznidazole in Treatment of Chagas Disease in Adults. Antimicrob Agents Chemother. 2010;54:4896.
Pund S, et al. In: Grumezescu AM ed. Nano- and Microscale Drug Delivery Systems. Elsevier; 2017:439-80.
Pushpakom S, et al. Drug repurposing: progress, challenges and recommendations. Nat Rev Drug Discov. 2019;18:41-58.
Quezada, C. Q. et al. Advances in nanocarriers as drug delivery systems in Chagas disease. International journal of nanomedicine. 2019;14:6407-24.
Ray K, et al. Life on the inside: the intracellular lifestyle of cytosolic bacteria. Nat Rev Microbiol. 2009;7:333-40.
Rial MS, et al. Elucidating the impact of low doses of nano-formulated benznidazole in acute experimental Chagas disease. PLOS Negl Trap Dis. 2017;11:e0006119.
Romero EL, et al. Nanotechnological approaches against Chagas disease. Adv Drug Deliv Rev. 2010;62:576-88.
Ryu, Y.-S., et al. "Reconstituting ring-rafts in bud-mimicking topography of model membranes." Nature communications 5.1 (2014): 1-8.
Sales Junior PA, et al. Experimental and Clinical Treatment of Chagas Disease: A Review. Am J Trop Med Hyg. 2017;97:1289-303.
Sanchez-Schmitz G, et al. "Development of newborn and infant vaccines." Science translational medicine 3.90 (2011): 90ps27-90ps27.
Sanchez-Valdez FJ, et al. Spontaneous dormancy protects Trypanosoma cruzi during extended drug exposure. eLife. 2018;7:e34039.
Santos EdS, et al. Tolerogenic Dendritic Cells Reduce Cardiac Inflammation and Fibrosis in Chronic Chagas Disease. Frontiers in immunology. 2020;11:488-.
Scott EA, et al. Dendritic cell activation and T cell priming with adjuvant- and antigen-loaded oxidation-sensitive polymersomes. Biomaterials. 2012;33:6211-9.
Scott, E. A., et al. "Overcoming immune dysregulation with immunoengineered nanobiomaterials." Annual Review of Biomedical Engineering 19 (2017): 57-84.
Shang, S., et al. "Induction of *Mycobacterium tuberculosis* lipid-specific T cell responses by pulmonary delivery of mycolic acid-loaded polymeric micellar Nanocarriers." Frontiers in immunology 9 (2018): 2709.
Shaw CD et al. Drug delivery: lessons to be learnt from Leishmania studies. Nanomedicine. 2014;9:1531-44.
Shenoda, B. B., et al. "Modulation of immune responses by exosomes derived from antigen-presenting cells." Clinical Medicine Insights: Pathology 9 (2016): CPath-S39925.
Smith SA, et al. The Endosomal Escape of Nanoparticles: Toward More Efficient Cellular Delivery. Bioconjugate Chem. 2019;30:263-72.
Speriando Da Silva GM, et al. Benznidazole treatment safety: the Médecins Sans Frontières experience in a large cohort of Bolivian patients with Chagas' disease. J Ant Chem. 2017;72:2596-601.
Stack, T, et al. "Modulation of Schlemm's canal endothelial cell stiffness via latrunculin loaded block copolymer micelles." Journal of Biomedical Materials Research Part A 106.7 (2018): 1771-1779.
Tanowitz HB, et al. "Developments in the management of Chagas cardiomyopathy." Expert review of cardiovascular therapy 13.12 (2015): 1393-1409.
Van Der Meel R, et al. Smart cancer nanomedicine. Nature Nanotechnology. 2019;14:1007-17.
Van Der Wel N, et al. M. tuberculosis and M. leprae Translocate from the Phagolysosome to the Cytosol in Myeloid Cells. Cell. 2007;129:1287-98.
Vasdekis, A. E., et al. "Precision intracellular delivery based on optofluidic polymersome rupture." ACS nano 6.9 (2012): 7850-7857.
Velluto D, et al. PEG-b-PPS Diblock Copolymer Aggregates for Hydrophobic Drug Solubilization and Release Cyclosporin A as an Example. Mol Pharmaceutics. 2008;5:632-42.
Ventola CL. Progress in Nanomedicine: Approved and Investigational Nanodrugs. P & T : a peer-reviewed journal for formulary management. 2017;42:742-55.
Viotti R, et al. Side effects of benznidazole as treatment in chronic Chagas disease: fears and realities. Expert Rev Anti Infect Ther. 2009;7:157-63.
Wang, C., et al. "In situ formed reactive oxygen species-responsive scaffold with gemcitabine and checkpoint nhibitor for combination therapy." Science translational medicine 10.429 (2018).
Yi S, et al., Tailoring Nanostructure Morphology for Enhanced Targeting of Dendritic Cells in Atherosclerosis. ACS Nano. 2016;10(12):11290-11303.
Yi S, et al. An Injectable Hydrogel Platform for Sustained Delivery of Anti-inflammatory Nanocarriers and Induction of Regulatory T Cells in Atherosclerosis. Frontiers in Bioengineering and Biotechnology. 2020;8:542.
Yi S, et al. "Surface engineered polymersomes for enhanced modulation of dendritic cells during cardiovascular immunotherapy." Advanced Functional Materials 29.42 (2019): 1904399.
Yi F, et al. (2016). Stretchable and waterproof self-charging power system for harvesting energy from diverse deformation and powering wearable electronics. ACS nano, 10(7), 6519-6525.
Zhao J, et al. Entry of nanoparticles into cells: The importance of nanoparticle properties. Polym Chem. 2018;9:259-72.

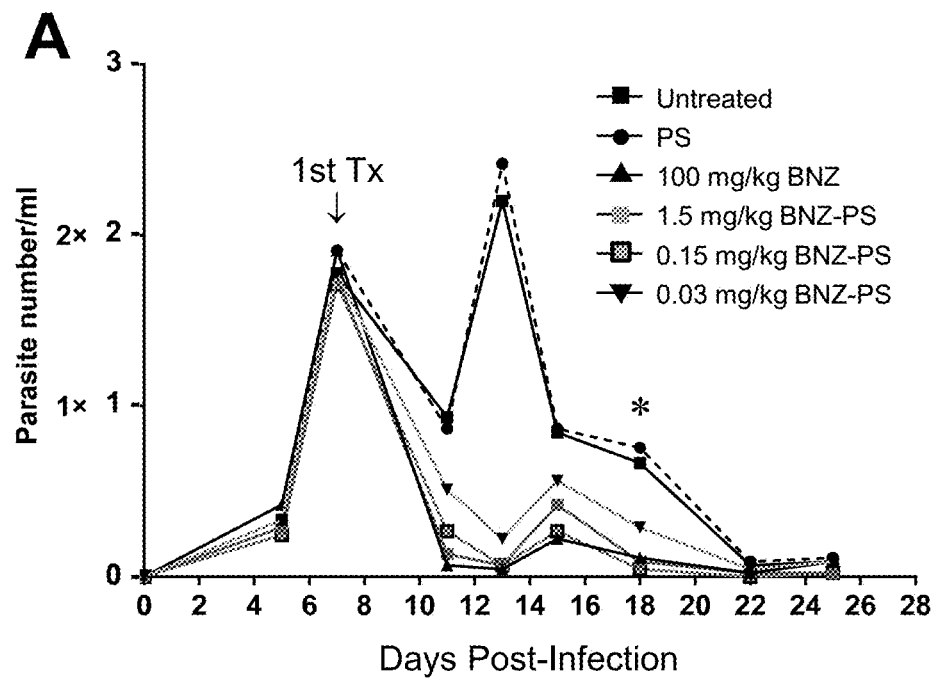
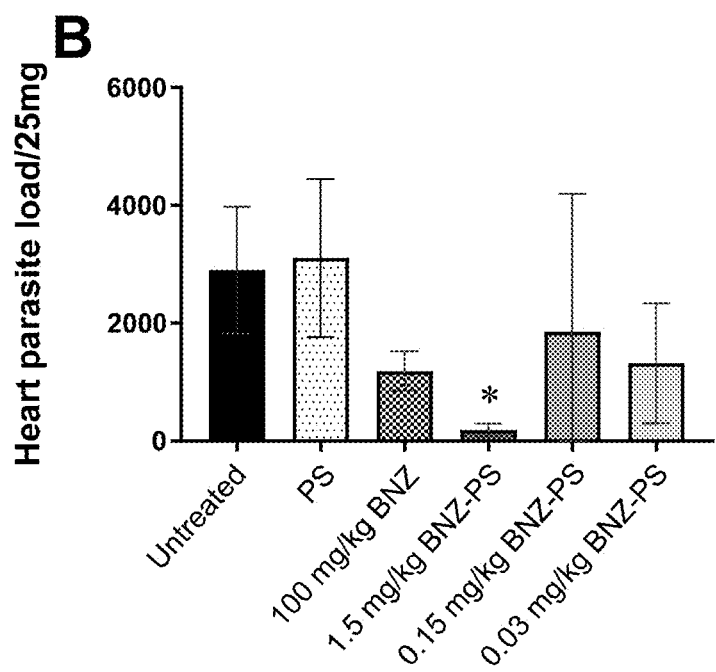
FIG. 3A-B

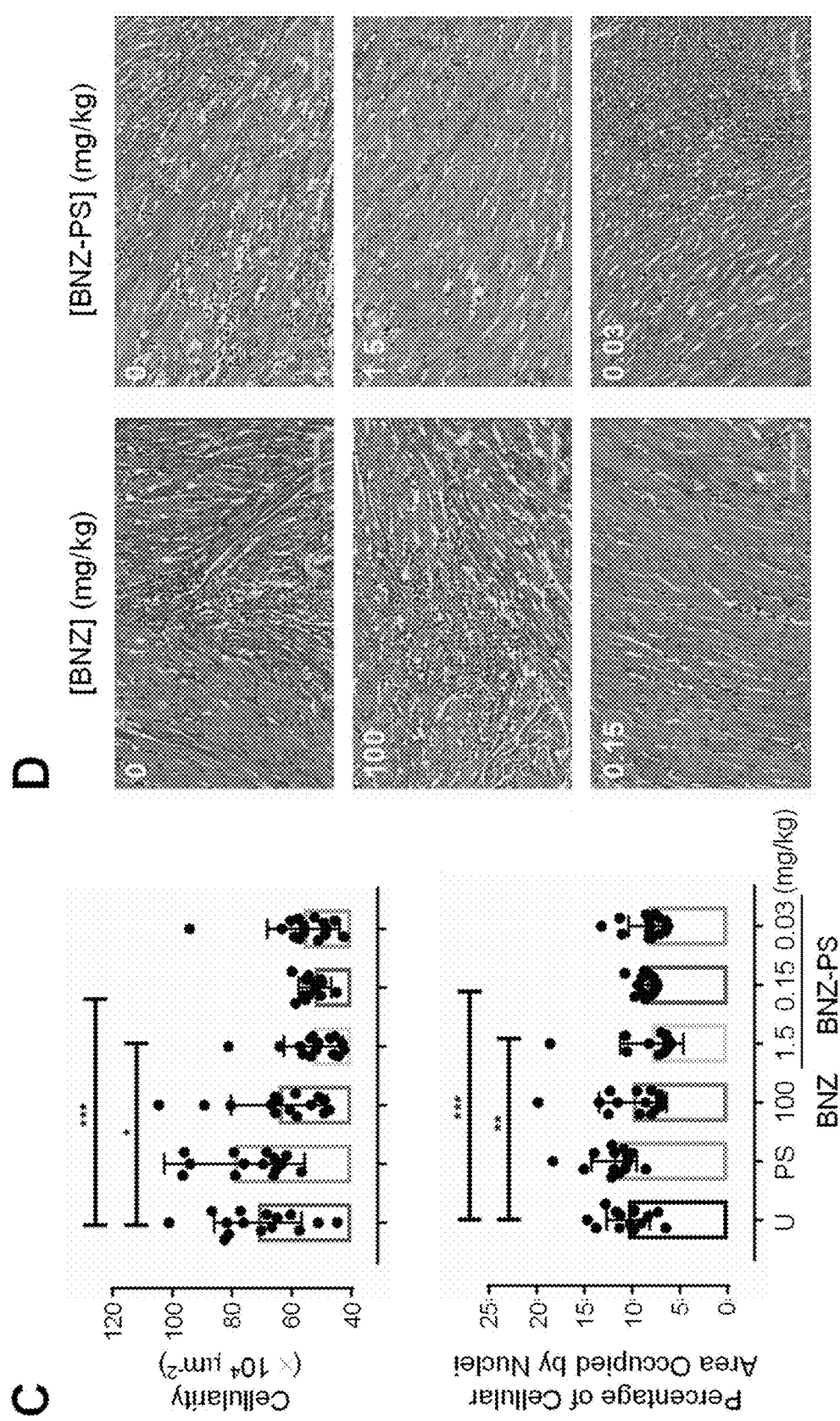
FIG. 3C-D

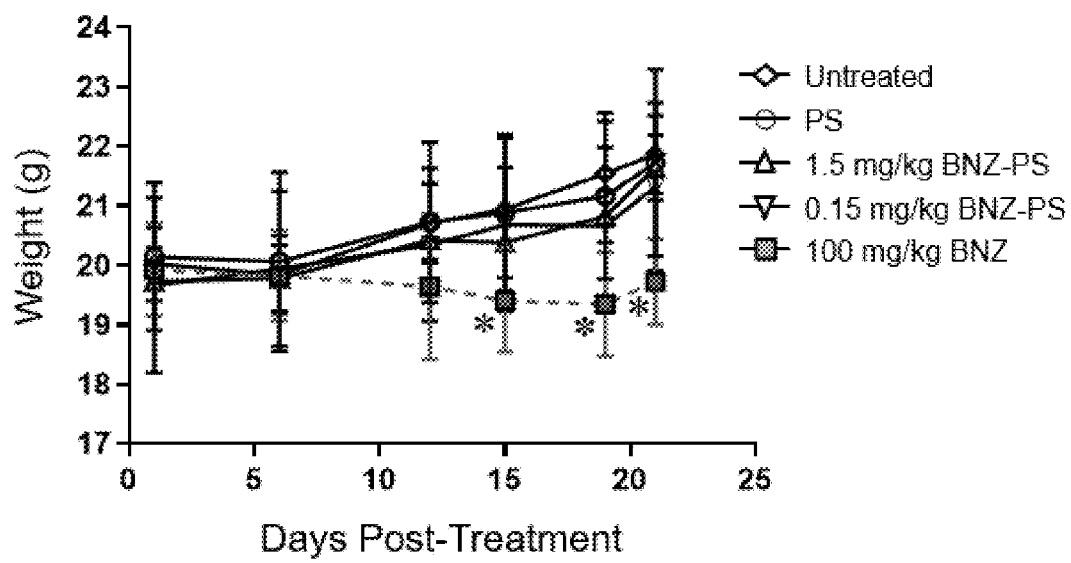
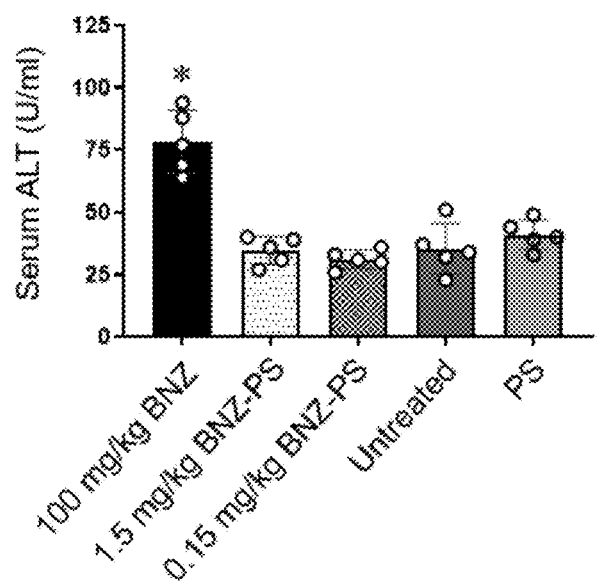
FIG. 4A-B

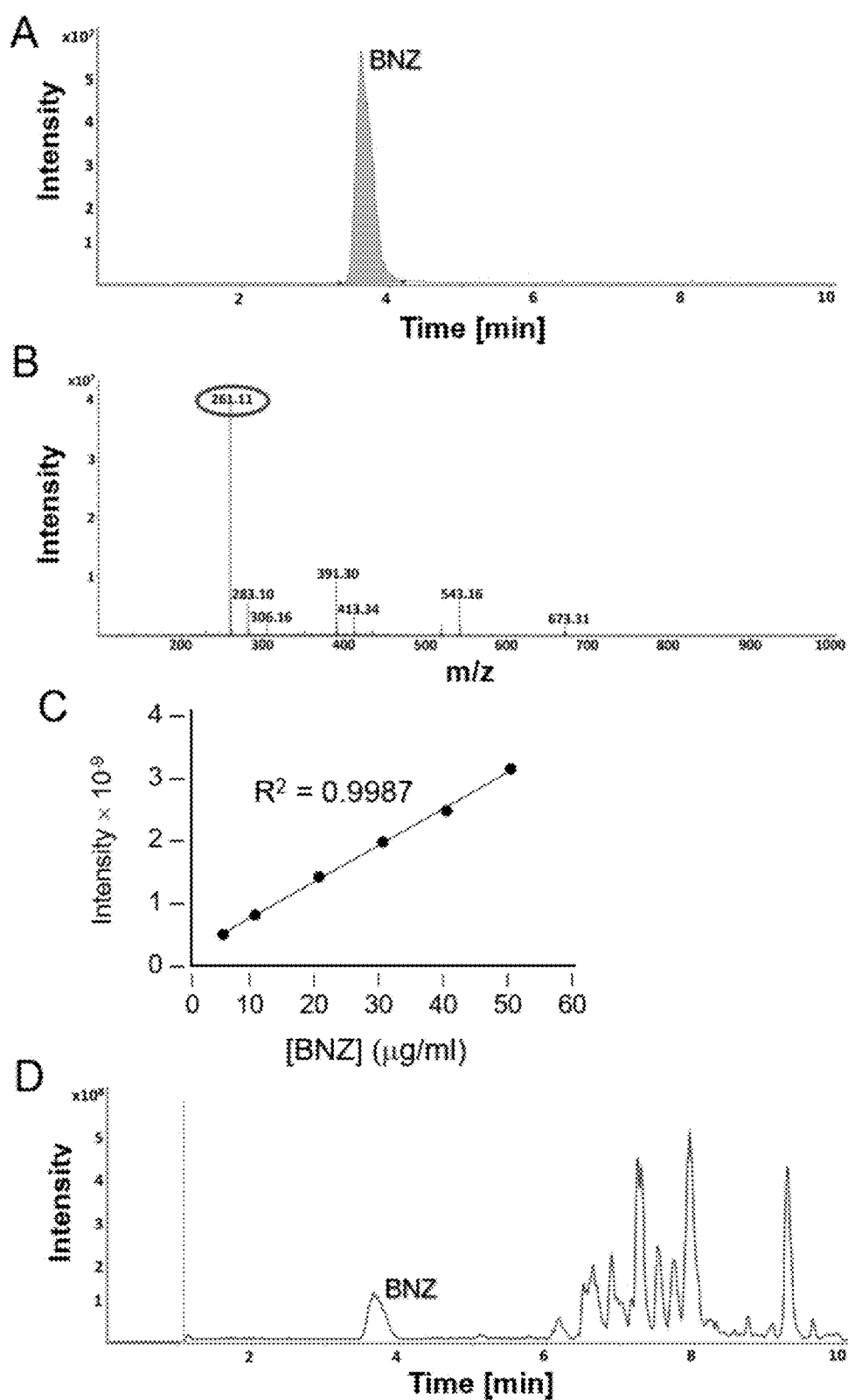
FIG. 5A-D

COMPOSITIONS AND METHODS OF USING PROPYLENE SULFIDE-BASED POLYMERS FOR TREATMENT OF CHAGAS DISEASE

CROSS-REFERENCE TO RELATED APPLICATIONS

This application claims priority to U.S. Provisional Application No. 62/880,013, filed Jul. 29, 2019, the contents of which are incorporated by reference.

STATEMENT REGARDING FEDERALLY SPONSORED RESEARCH

This invention was made with government support under grant numbers AI144529 and HL132390 awarded by the National Institutes of Health. The government has certain rights in the invention.

REFERENCE TO A SEQUENCE LISTING SUBMITTED VIA EFS-WEB

The content of the ASCII text file of the sequence listing named "702581_01793_ST25.txt" which is 0.751 kb in size was created on Jul. 28, 2020 and electronically submitted via EFS-Web herewith the application is incorporated herein by reference in its entirety.

BACKGROUND OF THE INVENTION

American Trypanosomiasis or Chagas disease (CD) is a vector-borne disease first described by the Brazilian sanitary physician Carlos Chagas, in 1909. After discovering the flagellate protozoan parasite, *Trypanosoma cruzi*, in sylvatic and domestic animals, human blood, and in the triatomine insect vector ("kissing" bug), Chagas deduced the essential aspects of the disease. At the beginning of the 20th century, CD was considered a rural endemic disease, strictly associated with the proximity between the insect vector and humans living in poor housing and sanitary conditions in rural areas of Latin America. However, in the 21st century, CD has spread to non-endemic areas, such as Canada, the USA, Europe, Australia, and Japan due to population migrations and the altered distribution and proliferation of triatomine bugs stimulated by climate change. As no vaccine is currently available, 65-100 million people live at risk of contracting a *T. cruzi* infection. Of those at risk, around 6-7 million people are infected and approximately 14,000 deaths are reported annually in endemic and non-endemic countries. These deaths typically occur as a consequence of heart failure induced by the *T. cruzi* infection. This alarming data is reflected in the CD status as a "neglected disease", which is still overlooked by drug developers as it mostly affects poor people in low-income countries.

Since 1912, several molecules have been experimentally tested against CD, from primitive arsenic and mercury derivatives to antibiotics, and more recently ergosterol synthesis inhibitors, all without successful results. Only two hydrophobic nitroimidazole pro-drugs, Benznidazole (BNZ) and Nifurtimox (Nfx), have been available to treat *T. cruzi*-infected patients since 1970. Despite the poor bioavailability and permeability, both drugs can reach up to 80% of efficacy when used during acute *T. cruzi* infections. However, the requirement for long-term treatment and the severe side effects, including allergic dermatitis, pruritus, gastrointestinal manifestations, and neuropathy, lead to the permanent withdrawal of treatment in 6 to 40% of patients receiving Nfx and 7 to 30% of those receiving BNZ.

There is a need for a Chagas treatment that is effective in treating *T. cruzi* infections without the severe side effects shown in the present treatment available treatments.

SUMMARY OF THE INVENTION

The present disclosure provides novel nanocarriers for treating Chagas disease. The nanocarriers comprise (a) poly (ethylene glycol)-block-poly(propylene sulfide) copolymers and (b) a therapeutic agent for treating Chagas disease. The therapeutic agent is selected from the group consisting of N-benzyl-2-(2-nitro-1H-imidazol-1-yl)acetamide (Benznidazole), N-(3-Methyl-1,1-dioxido-4-thiomorpholinyl)-1-(5-nitro-2-furyl)methanimine (Nifurtimox), 1-Methyl-2-{[4-methylsulfanyl)phenoxy]methyl}-5-nitro-1H-imidazole (Fexinidazole), 4-[4-[4-[4-[[(3R,5R)-5-(2,4-difluorophenyl) tetrahydro-5-(1H-1,2,4-triazol-1-ylmethyl)-3-furanyl] methoxy]phenyl]-1-piperazinyl]phenyl]-2-[(1S,2S)-1-ethyl-2-hydroxypropyl]-2,4-dihydro-3H-1,2,4-triazol-3-one (Posaconazole), cysteine protease inhibitors, parasite proteasome inhibitors such as N-[4-fluoro-3-(6-pyridin-2-yl-[1,2,4]triazolo[1,5-a]pyrimidin-2-yl)phenyl]-2,4-dimethyl-1,3-oxazole-5-carboxamide.

In another aspect, the disclosure provides a pharmaceutical composition comprising the nanocarrier described herein and one or more pharmaceutically acceptable excipients.

In a further aspect, the disclosure provides a method of treating a *Trypanosoma cruzi* infection in a subject in need thereof, the method comprising administering to the subject a therapeutically effective amount a pharmaceutical composition comprising a nanocarrier comprising poly(ethylene glycol)-block-poly(propylene sulfide) copolymer; and a therapeutic agent for treating Chagas disease.

12. The method of claim 11, wherein the therapeutic agent for treating Chagas disease is selected from the group consisting of N-benzyl-2-(2-nitro-H-imidazol-1-yl)acetamide (Benznidazole), N-(3-Methyl-1,1-dioxido-4-thiomorpholinyl)-1-(5-nitro-2-furyl)methanimine (Nifurtimox), 1-Methyl-2-{[4-methylsulfanyl)phenoxy]methyl}-5-nitro-1H-imidazole (Fexinidazole), 4-[4-[4-[4-[[(3R,5R)-5-(2,4-difluorophenyl)tetrahydro-5-(1H-1,2,4-triazol-1-ylmethyl)-3-furanyl]methoxy]phenyl]-1-piperazinyl]phenyl]-2-[(1S, 2S)-1-ethyl-2-hydroxypropyl]-2,4-dihydro-3H-1,2,4-triazol-3-one (Posaconazole), cysteine protease inhibitors, parasite proteasome inhibitors such as N-[4-fluoro-3-(6-pyridin-2-yl-[1,2,4]triazolo[1,5-a]pyrimidin-2-yl)phenyl]-2,4-dimethyl-1,3-oxazole-5-carboxamide.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3. Benznidazole polymersomes are more potent than free benznidazole against *T. cruzi* in vivo. (A) Effective suppression of parasitemia by BNZ and BNZ-PS. Mice were infected with *T. cruzi* at d0 and treated with BNZ or various doses of BNZ-PS after parasitemia had reached approximately $2 \times 10^5$ ml$^{-1}$ on d7. Parasitemia was monitored every few days through the end of the experiment on d25. (B) Mice were sacrificed at the end of the experiment and cardiac parasitosis was quantitated by qPCR. (C) Cardiac inflammation was quantitated in heart sections two ways—by total cellularity and by the percentage of cellular area occupied by nuclei. (D) Representative cardiac histology at the end of the experiment. Bar=100 µM.

FIG. 4. Benznidazole polymersomes are much less toxic than free benznidazole. Mice were treated with BNZ (100 mg/kg) or BNZ-PS (1.5 or 0.15 mg/kg), plus controls. (A) Mice treated with BNZ, but not BNZ-PS, lose weight during 3 weeks of treatment. Weights were determined every few days. (B) Mice treated with BNZ show hepatotoxicity as reflected by increased serum ALT at d21. Serum ALT was also measured and did not show significant elevation in any mouse.

FIG. 5 Validation of BNZ loading within BNZ-PS. (A) Representative chromatogram and (B) positive ion mass spectrum of BNZ standards. The BNZ peak is indicated at m/z of ~261. (C) Calibration curve of BNZ standards. (D) Representative chromatogram of BNZ-PS displaying a BNZ peak at the same elution time as in the standard (A).

DETAILED DESCRIPTION OF THE INVENTION

Figure 1:
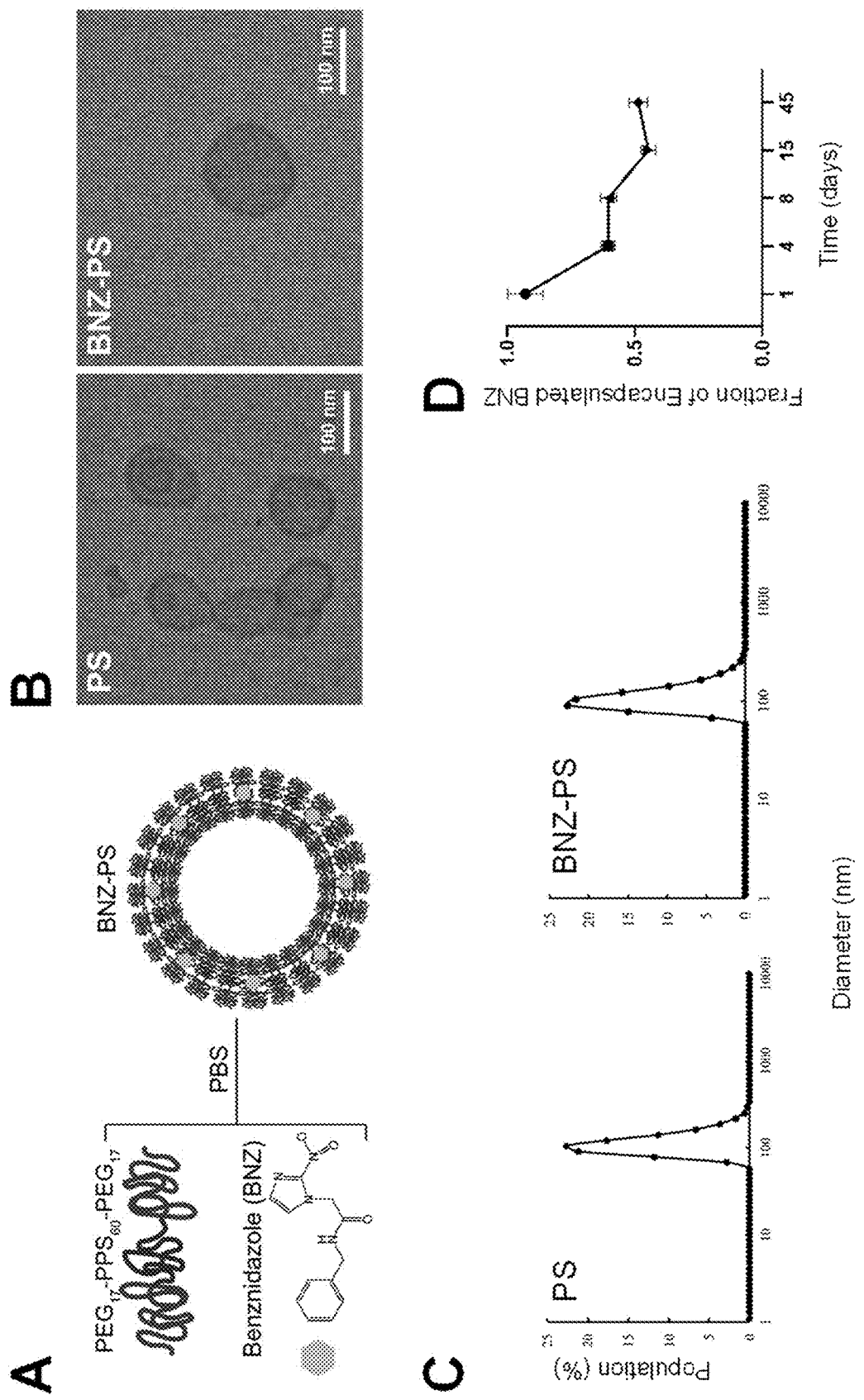
FIG. 1 Benznidazole polymersomes are 100 nm particles with good in vitro stability. (A) Benznidazole (BNZ) was loaded into polymersomes (BNZ-PS) by the thin film hydration method. (B) Representative cryo transmission electron microscopy images of PS and BNZ-PS. (C) The diameters of PS and BNZ-PS are approximately 100 nm as determined by dynamic light scattering analysis. (D) The stability of BNZ-PS was determined by incubating the particles in PBS at room temperature and subtracting the fraction of BNZ found free in solution over time.

The present invention has been described in terms of one or more preferred embodiments, and it should be appreciated that many equivalents, alternatives, variations, and modifications, aside from those expressly stated, are possible and within the scope of the invention.

The present disclosure describes nanocarriers for treating Chagas disease. The nanocarriers comprise poly(ethylene glycol)-block-poly(propylene sulfide) copolymer and a therapeutic agent for treating Chagas disease.

Chagas disease, or American trypanosomiasis, is a tropical parasitic disease caused by the protozoan *Trypanosoma cruzi*. It is spread mostly by insects known as triatominae or kissing bugs. These insects are known by a number of local names, including: vinchuca in Argentina, Bolivia, Chile and Paraguay, barbeiro (the barber) in Brazil, pito in Colombia, chinche in Central America, and chipo in Venezuela. The disease may also be spread through blood transfusion, organ transplantation, eating food contaminated with the parasites, and by vertical transmission (from a mother to her fetus). Diagnosis of early disease is by finding the parasite in the blood using a microscope. Chronic disease is diagnosed by finding antibodies for *T. cruzi* in the blood.

The term "nanocarrier" refers to a nanomaterial used as a transport module for another substance. For example, the nanocarriers disclosed herein may be used as a transport module for therapeutic agents for treating Chagas disease. The nanocarriers disclosed herein may be used as components of pharmaceutical compositions for treating Chagas disease. In some embodiments, the nanocarriers disclosed herein are composed of a poly(ethylene glycol)-block-poly(propylene sulfide) copolymer and a therapeutic agent for treating Chagas disease.

Poly(ethylene glycol)-block-poly(propylene sulfide) copolymers (PEG-b-PPS) can be prepared via known methods, for example those described in Allen, S. et al., Facile assembly and loading of theranostic polymersomes via multi-impingement flash nanoprecipitation *J. Control. Release* 2017. 262: p. 91-103 and in U.S. Pat. No. 10,633,493, each of which is incorporated herein by reference in its entirety with regard to the method of preparing the copolymers. An exemplary synthesis is described in the Examples. For example, the PEG-b-PPS are prepared via the anionic ring-opening polymerization of propylene sulfide initiated by PEG thioacetate and end-capped with PEG mesylate. The PEG-b-PPS are purified by precipitation in methanol.

To obtain the nanocarriers described herein, the PEG-b-PPS are loaded with a therapeutic agent for treating Chagas disease. The nanocarriers can be prepared/loaded, for example, by any viable method of nanoparticle fabrication and/or self-assembly, including thin film rehydration, flash-nanoprecipitation, microfluidics, or solvent extraction To load the PEG-b-PPS with a therapeutic agent, via thin film rehydration, the PEG-b-PPS are dissolved with therapeutic agents in one or more organic solvents. The resulting solution is dehydrated by adding an aqueous solution (e.g., a buffer such as phosphate-buffered saline) to the mixture which can be shaken overnight, followed by extrusion (e.g., using a syringe filter). Unloaded therapeutic agents can be removed either via exclusion column purification or dialysis.

Nanocarriers can be characterized for size distribution via dynamic light scattering (DLS) and nanoparticle tracking analysis (NTA), and for morphology via cryogenic transmission electron microscopy (cryoTEM). Therapeutic agent loading and encapsulation efficiencies can be characterized via liquid chromatography mass spectrometry.

A variety of types of nanocarriers can be prepared by varying the degree of propylene sulfide polymerization, oxidation or branching. For example, nanocarriers may be in the form of polymersomes (PEG weight fraction of about 0.25 to about 0.45), micelles (PEG weight fraction above 0.45), biocontinuous nanospheres (PEG weight fraction below 0.25), filomicelles (PEG weight fraction of about 0.35 to about 0.45), polypropylene sulfone nanogels (above 90% oxidized PPS homopolymer), or polymersomes assembled from branched raft polymerized poly(oligo(ethylene glycol) methyl ether methacrylate)-b-poly(oligo(propylenesulfide) methacrylate) (POEGMA-POPSMA[1-5] In some embodiments, the block copolymer has a PEG weight fraction of about 0.36.

In some embodiments, the nanocarrier is a polymersome having an aqueous core and hydrophobic and hydrophilic regions of the lipid bilayer surrounding the aqueous core. The polymersome nanocarrier can have a PEG weight fraction of about 0.25 to about 0.45, e.g., 0.36. The polymersome nanocarrier may have a diameter of about 10 nm to about 300 nm, alternatively from about 30 nm to about 150 nm in diameter, alternatively from about 30 nm to about 60 nm, alternatively from about 60 nm to about 90 nm, alternatively from about 100 nm to about 150 nm in diameter. In some embodiments, the size of the polymersome remains about the same when it is loaded with a Chagas therapeutic agent compared to the size of an unloaded polymersome made from the same copolymer. In one embodiment, the polymersome comprises a vesicular polymer membrane composed of $PEG_{17}$-$PPS_{60}$-$PEG_{17}$.

In some embodiments, the nanocarrier is a bicontinuous nanosphere (BCN) characterized by two continuous phases; (i) a cubic lattice of aqueous channels that traverse (ii) an extensive hydrophobic interior volume. Based on small angle X-ray scattering (SAXS) analysis, BCN have primitive type cubic internal organization (Im3m) as confirmed by Bragg peaks with relative spacing ratios at √2, √4, and √6. BCNs are the polymeric equivalent of lipid cubosomes and are lyotropic. BCN can incorporate both hydrophobic and hydrophilic therapeutic agents. BCNs can be prepared via known methods, for examples those described in Allen, S. et al., Benchmarking bicontinuous nanospheres against polymersomes for in vivo biodistribution and dual intracellular delivery of lipophilic and water soluble payloads. *ACS Appl. Mater. Interfaces* 2018, 10, 40, 33857-33866, which is incorporated herein by reference.

In some embodiments, the nanocarrier is a micelle or a filomicelle having a hydrophobic/lipophilic core and a hydrophilic exterior. Micelle or filomicelle nanocarriers have a spherical morphology and are typically smaller (e.g., less than 50 nm) than polymersomes and the hydrophobic core can be loaded with a therapeutic agent. The micelles suitably have a PEG weight fraction of about 0.35 to about 0.45. Micelles or filomicelles can be prepared via known methods, for example those described in Karabin, N. B. Allen, S., Kwon, H. et al. Sustained micellar delivery via inducible transitions in nanostructure morphology. *Nat Commun* 9, 624 (2018), which is incorporated herein by reference.

Other suitable preparation methods of the nanocarriers disclosed herein can be prepared via known methods, e.g., Du, F., et al., (2019). Homopolyner Self-Assembly via Poly(propylene Sulfone) Networks. ChemRxiv. Preprint; Du F. et a., Sequential intracellular release of water-soluble cargos from Shell-crosslinked polymersomes. *J Control Release*. 2018; 282:90-100; and Yj S., et al, Tailoring Nanostructure Morphology for Enhanced Targeting of Dendritic Cells in Atherosclerosis. *ACS Nano*. 2016; 10(12): 11290-11303, each of which are incorporated herein by reference in their entirety.

The nanocarrier further comprises a therapeutic agent for treating Chagas disease. The therapeutic agent may be selected from the group consisting of N-benzyl-2-(2-nitro-TH-imidazol-1-yl)acetamide (Benznidazole) and N-(3-Methyl-1,1-dioxido-4-thiomorpholinyl)-1-(5-nitro-2-furyl) methanimine (Nifurtimox). In some embodiments, the therapeutic agent may be selected from the group consisting of N-benzyl-2-(2-nitro-H-imidazol-1-yl)acetamide (Benznidazole), N-(3-Methyl-1,1-dioxido-4-thiomorpholinyl)-1-(5-nitro-2-furyl)methanimine (Nifurtimox), 1-Methyl-2-{[4-methylsulfanyl)phenoxy]methyl}-5-nitro-TH-imidazole (Fexinidazole), 4-[4-[4-[4-[[(3R,5R)-5-(2,4-difluorophenyl)tetrahydro-5-(1H-1,2,4-triazol-1-ylmethyl)-3-furanyl]methoxy]phenyl]-1-piperazinyl]phenyl]-2-[(1S,2S)-1-ethyl-2-hydroxypropyl]-2,4-dihydro-3H-1,2,4-triazol-3-one (Posaconazole), cysteine protease inhibitors, parasite proteasome inhibitors such as N-[4-fluoro-3-(6-pyridin-2-yl-[1,2,4]triazolo[1,5-a]pyrimidin-2-yl)phenyl]-2,4-dimethyl-1,3-oxazole-5-carboxamide (GNF6702). In some embodiments, the therapeutic agent is N-benzyl-2-(2-nitro-1H-imidazol-1-yl)acetamide (Benznidazole). The inventors have surprisingly found that encapsulation of the therapeutic agent for treating Chagas disease can be administered at substantially lower levels than the free form drug, reducing unwanted and unnecessary side effects, allowing for longer term use of the treatment.

The nanocarrier may comprise any suitable molar ratio of therapeutic agent:core necessary to achieve the desired effect. For example, the nanocarrier may comprise a molar ratio of therapeutic agent:poly(ethylene glycol)-block-poly (propylene sulfide) copolymer of 0.001%-50%. For example, the molar ratio may be 0.001%, 0.005%, 0.01%, 0.5%, 1%, 2%, 3%, 4%, 5%, 6%, 7%, 8%, 9%, 10%, 20%, 30%, 40%, or 50%. In some embodiments, the molar ratio of therapeutic agent:poly(ethylene glycol)-block-poly(propylene sulfide) copolymer is 1%-10%. %. In particular embodiments, the molar ratio of therapeutic agent:poly (ethylene glycol)-block-poly(propylene sulfide) copolymer is 1%.

In some embodiments, the nanocarriers present an encapsulation efficiency (% EE) of greater than 0% to about 100%. In some embodiments, the nanocarriers present an encapsulation efficiency (% EE) of about 20% to about 40%. In some embodiments, the nanocarriers present a loading efficiency (% LE) of greater than 0% to 100%. In some embodiments, the nanocarriers present a % LE of about 0.5 to about 2% w/w.

In some embodiments, nanocarriers comprising the therapeutic agent Benznidazole may enable delivery of significantly lower therapeutically effective dosages of Benznidazole compared to the dosages required for therapeutic efficacy of Benznidazole alone. For example, a typical free Benznidazole $IC_{50}$ may be about 33 μM. Benznidazole loaded in nanocarrier formulations has an estimated $IC_{50}$ of 3.5 μM, a concentration nearly 10 times lower. In a subject, while Benznidazole may typically be administered at a dosage of about 100 mg/kg, loaded-Benznidazole nanocarrier of the present invention can be administered at a dosage between about 0.025 mg/kg and about 2 mg/kg (For example, FIG. 5A). In some embodiments, the loaded-Benznidazole nanocarrier can be administered at a dosage of 0.025 mg/kg to 100 mg/kg. In some embodiments, the loaded-Benznidazole nanocarrier can be administered at a dosage of 0.025 mg/kg, or 0.03 mg/kg, or 0.05 mg/kg, or 0.10 mg/kg, or 0.15 mg/kg, or 0.30 mg/kg, to 0.5 mg/kg, or 0.75 mg/kg, or 1.0 mg/kg, or 1.25 mg/kg, or 1.5 mg/kg, or 1.75 mg/kg, or 2.0 mg/kg. In some embodiments, the loaded-Benznidazole nanocarrier can be administered at a dosage of 2.0 mg/kg, or 5.0 mg/kg, or 10 mg/kg, or 20 mg/kg, or 30 mg/kg, or 40 mg/kg, or 50 mg/kg, or 60 mg/kg, or 70 mg/kg, or 80 mg/kg, or 90 mg/kg, or 100 mg/kg. In some embodiments, the lower therapeutically effective dose of Benznidazole when administered in a nanocarrier formulation is at least 500, at least 1000, at least 10,000, at least 25,000, or at least 50,000 times lower than the therapeutically effective dose of free Benznidazole (when administered orally). In accordance with such embodiments, nanocarriers comprising Benznidazole may be safely used in a subject with improved efficacy and safety.

In some embodiments, the loaded-Nifurtimox nanocarrier can be administered at a dosage of 0.025 mg/kg to 100 mg/kg. In some embodiments, the loaded-Nifurtimox nanocarrier can be administered at a dosage of 0.025 mg/kg, or 0.03 mg/kg, or 0.05 mg/kg, or 0.10 mg/kg, or 0.15 mg/kg, or 0.30 mg/kg, to 0.5 mg/kg, or 0.75 mg/kg, or 1.0 mg/kg, or 1.25 mg/kg, or 1.5 mg/kg, or 1.75 mg/kg, or 2.0 mg/kg. In some embodiments, the loaded-Nifurtimox nanocarrier can be administered at a dosage of 2.0 mg/kg, or 5.0 mg/kg, or 10 mg/kg, or 20 mg/kg, or 30 mg/kg, or 40 mg/kg, or 50 mg/kg, or 60 mg/kg, or 70 mg/kg, or 80 mg/kg, or 90 mg/kg, or 100 mg/kg. In some embodiments, the lower therapeutically effective dose of Nifurtimox when administered in a nanocarrier formulation is at least 500, at least 1000, at least 10,000, at least 25,000, or at least 50,000 times lower than the therapeutically effective dose of free Nifurtimox (when administered orally). In accordance with such embodiments, nanocarriers comprising Nifurtimox may be safely used in a subject with improved efficacy and safety.

In some embodiments, the nanocarriers comprising the therapeutic agent are able to achieve the same immunomodulatory effects at a lower therapeutically effective dose compared the therapeutically effective dose required for free therapeutic agent (i.e. the therapeutic agent in the absence of the nanocarrier), therefore allowing therapeutic efficacy with minimized or null side effects in the subject. Side effects typically associated with Chagas disease treatments may include, but are not limited to, neuropathy, dermatitis, pruritus, gastrointestinal manifestations, anorexia, bone marrow suppression, headache, weight loss, hepatic function alteration, among others.

The disclosed nanocarriers are advantageous over current therapies on the market for a variety of reasons. The polymers used in the nanocarriers, poly(ethylene glycol) and poly(propylene sulfide) have been widely proven to be inert.

The nanocarriers disclosed herein may also be incorporated into pharmaceutical compositions. The disclosed nanocarriers or pharmaceutical compositions comprising the same may be used in methods of treating Chagas disease in a subject in need thereof. The pharmaceutical compositions may further comprise one or more pharmaceutically acceptable excipients. The pharmaceutically acceptable excipients will be dependent on the mode of administration to be used. Suitable modes of administration include, without limitation: topical, subcutaneous, transdermal, intradermal, intralesional, intraarticular, intraperitoneal, intravesical, transmucosal, gingival, intradental, intracochlear, transtympanic, intraorgan, epidural, intrathecal, intramuscular, intravenous, intravascular, intraosseus, periocular, intratumoral, intracerebral, and intracerebroventricular administration. In some embodiments, the disclosed pharmaceutical compositions are administered parenterally. In some embodiments, parenteral administration is by intrathecal administration, intracerebroventricular administration, or intraparenchymal administration. In particular embodiments, the disclosed pharmaceutical compositions are administered subcutaneously. In particular embodiments, the disclosed pharmaceutical compositions are administered intravenously. The disclosed pharmaceutical compositions herein can be administered as the sole active agent or in combination with other pharmaceutical agents such as other agents used in the treatment of Chagas disease in a subject.

The amount of the disclosed nanocarriers or pharmaceutical compositions comprising the same to be administered is dependent on a variety of factors, including the severity of the condition, the age, sex, and weight of the subject, the frequency of administration, the duration of treatment, and the like. The disclosed nanocarriers or pharmaceutical compositions may be administered at any suitable dosage, frequency, and for any suitable duration necessary to achieve the desired therapeutic effect, i.e., to treat Chagas disease. The disclosed nanocarriers or pharmaceutical compositions may be administered once per day or multiple times per day. Alternatively and preferably, the nanocarriers or pharmaceutical compositions may be administered once per week for at least 2 weeks. In other examples, the nanocarriers or pharmaceutical compositions may be administered once per day, twice per day, or three or more times per day. The disclosed nanocarrier or pharmaceutical compositions may be administered daily, every other day, every three days, every four days, every five days, every six days, once per week, once every two weeks, or less than once every two weeks. The nanocarriers or pharmaceutical compositions may be administered for any suitable duration to achieve the desired therapeutic effect, i.e., treat the Chagas disease. For example, the nanocarriers or pharmaceutical compositions may be administered to the subject for one day, two days, three days, four days, five days, six days, seven days, eight days, nine days, ten days, eleven days, twelve days, thirteen days, two weeks, one month, two months, three months, six months, 1 year, or more than 1 year. In some embodiments, the nanocarriers or pharmaceutical compositions may be administered for 14 days. In some embodiments, the nanocarriers or pharmaceutical compositions may be administered for 60 days. In some embodiments, the pharmaceutical composition or nanocarrier may be administered once per week. In some embodiments, the pharmaceutical composition or nanocarrier may be administered once per week for 60 days.

Any suitable dose of the disclosed nanocarriers or pharmaceutical compositions comprising the same may be used. Suitable doses will depend on the therapeutic agent, intended therapeutic effect, body weight of the individual, age of the individual, and the like. In general, suitable dosages of the disclosed nanocarriers or pharmaceutical compositions comprising the same may range from about 0.025 mg nanocarrier/kg body weight to 200 mg nanocarrier/kg body weight. For example, suitable dosages may be about 0.025 mg/kg, or 0.03 mg/kg, or 0.05 mg/kg, or 0.10 mg/kg, or 0.15 mg/kg, or 0.30 mg/kg, to 0.5 mg/kg, or 0.75 mg/kg, or 1.0 mg/kg, or 1.25 mg/kg, or 1.5 mg/kg, or 1.75 mg/kg, or 2.0 mg/kg. In some embodiments, the suitable doses may be 1 mg nanocarrier/kg body weight, or 3 mg/kg, or 5 mg/kg, or 10 mg/kg, or 25 mg/kg, or 50 mg/kg, or 75 mg/kg, or 100 mg/kg, or 125 mg/kg, or 150 mg/kg, or 175 mg/kg, or 200 mg/kg.

In some embodiments, the pharmaceutical composition or nanocarrier may be administered intravenously.

The present disclosure also provides in some embodiments methods of treating *Trypanosoma cruzi* infection in a subject in need thereof, the method comprising administering to the subject a therapeutically effective amount a pharmaceutical composition comprising a nanocarrier comprising poly(ethylene glycol)-block-poly(propylene sulfide) copolymer; and a therapeutic agent for treating Chagas disease.

As used herein, the terms "treat," "treatment," and "treating" refer to reducing the amount or severity of a particular condition, disease state (e.g., Chagas disease), or symptoms thereof, in a subject presently experiencing or afflicted with the condition or disease state. The terms do not necessarily indicate complete treatment (e.g., total elimination of the condition, disease, or symptoms thereof). "Treatment," encompasses any administration or application of a therapeutic or technique for a disease (e.g., in a mammal, including a human), and includes inhibiting the disease, arresting its development, relieving the disease, causing regression, or restoring or repairing a lost, missing, or defective function; or stimulating an inefficient process.

The severity and course of a *T. cruzi* infection is highly variable, based on many factors, including the age at which a person became infected, the way in which a person acquired the infection, the particular virulence of the *T. cruzi* strain involved in the infection and the immunogenetics of the individual person. There are two phases of Chagas disease: the acute phase, which occurs shortly after an initial infection, and the chronic phase, that develops over many years, even decades. Both phases can be symptom free or life threatening. During the acute phase, which lasts for the first few weeks or months after infection, a person often has no symptoms at all, by may have nonspecific symptoms such as fever, fatigue, body aches, headache, rash, loss of appetite, diarrhea, and vomiting. Because these symptoms may result from many, more common illnesses, most people do not realize that the symptoms are from *T. cruzi* infection. However, a physician may suspect Chagas disease, particularly in an area of high disease prevalence, if there is also mild hepatosplenomegaly, lymphadenopathy or erythema or swelling at the site of the bite (Chagoma), or preioribital edema upon conjunctival infection (Romaña's sign). Even if a person develops symptoms during the acute phase, they usually feel well within a few weeks, but if the person is not treated with antiparasitic medication, the infection is lifelong. Rarely, young children (less than 5%) die from acute myocarditisor meningoencephalitis. The acute phase also can be severe in people with immunosuppressed individuals, such as patients taking chemotherapy or those with advanced HIV infection. During the chronic phase, which can last for decades or even for the entirety of someone's lifetime, most people have no signs or symptoms of infection. Approximately 30 percent of infected people will eventually develop cardiac complications, which can include cardiomegaly, cardiac arrhythmias, heart failure or cardiac sudden death or gastrointestinal complications, which can include an enlarged esophagus (megaesophagus) or colon (megacolon), leading to achalasia and/or intractable constipation.

The term "subject" or "patient" are used herein interchangeably to refer to a mammal, preferably a human, to be treated by the methods and compositions described herein. "Mammals" means any member of the class Mammalia including, but not limited to, humans, non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Preferably, the subject is a human. In some embodiments, the subject is a mammal having Chagas disease or been infected with *Trypanosoma cruzi*. The term "subject" does not denote a particular age or sex. In one specific embodiment, a subject is a mammal, preferably a human. In a suitable embodiment, the subject is a human having Chagas disease or been infected with *Trypanosoma cruzi*.

The use herein of the terms "including," "comprising," or "having," and variations thereof, is meant to encompass the elements listed thereafter and equivalents thereof as well as additional elements. Embodiments recited as "including," "comprising" or "having" certain elements are also contemplated as "consisting essentially of" and "consisting of" those certain elements.

As used herein, "about" means within 5-10% of a stated concentration range or within 5-10% of a stated number.

It should be apparent to those skilled in the art that many additional modifications beside those already described are possible without departing from the inventive concepts. In interpreting this disclosure, all terms should be interpreted in the broadest possible manner consistent with the context. Variations of the term "comprising" should be interpreted as referring to elements, components, or steps in a non-exclusive manner, so the referenced elements, components, or steps may be combined with other elements, components, or steps that are not expressly referenced. Embodiments referenced as "comprising" certain elements are also contemplated as "consisting essentially of" and "consisting of" those elements. The term "consisting essentially of" and "consisting of" should be interpreted in line with the MPEP and relevant Federal Circuit's interpretation. The transitional phrase "consisting essentially of" limits the scope of a claim to the specified materials or steps "and those that do not materially affect the basic and novel characteristic(s)" of the claimed invention. "Consisting of" is a closed term that excludes any element, step or ingredient not specified in the claim. The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

The present invention has been described in terms of one or more preferred embodiments, and it should be appreciated that many equivalents, alternatives, variations, and modifications, aside from those expressly stated, are possible and within the scope of the invention.

The following Examples are offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

EXAMPLE 1

Introduction

American Trypanosomiasis or Chagas disease (CD) is a vector-borne disease first described by the Brazilian sanitary physician Carlos Chagas, in 1909 (1). After discovering the flagellate protozoan parasite, *Trypanosoma cruzi*, Chagas was able to deduce the entire complex parasite life cycle, clinical symptoms, and social impact of CD (2). At the beginning of the 20th century, CD was considered a rural endemic disease, strictly associated with the proximity between the insect vector and humans living in poor housing and sanitary conditions in Latin America (3). However, in the 21st century, CD has spread to non-endemic areas, such as Canada, the USA, Europe, Australia, and Japan due to population migrations and the altered proliferation of triatomine bugs stimulated by climate change (4-6). As no vaccine is currently available, 6-7 million people are infected worldwide and approximately 14,000 deaths are reported annually in endemic and non-endemic countries as a consequence of heart failure induced by the *T. cruzi* infection (7).

Only two hydrophobic nitroimidazole pro-drugs, Benznidazole (BNZ) and Nifurtimox (Nfx), have been available to treat *T. cruzi*-infected patients since 1970 (8). Despite the poor bioavailability and permeability (9), both drugs can reach up to 80% of efficacy when used during acute *T. cruzi* infections. However, the requirement for long-term treatment and the severe side effects, including neutropenia, nausea, vomiting and diarrhea, weight loss, hypersensitivity skin reactions and hives, may lead to the permanent withdrawal of treatment (10). CD treatment is still controversial for chronically-infected patients as the limited efficacy rate of BNZ and Nfx, from 5-20% (11) does not outweigh the potential risks associated with the treatment. This alarming data is reflected in the CD status as a "neglected disease", which is still overlooked by drug developers as it mostly affects poor people in low-income countries (4,12).

More than a century since CD discovery, the search for effective and safe drugs remains a challenge. As an obligate intracellular parasite, *T. cruzi* infects many nucleated cells, including macrophages and dendritic cells (DCs) limiting their activation/maturation and the antigen-presenting capacity, as a immune evasion strategy (10). Protected within the host cells, such as myoblasts, parasites divide intensively generating pseudocyst structures into the cytoplasm (13). Thus, drug candidates against CD must present high solubility, permeability, and selectivity to cross the cell membranes to kill the parasite without damaging the host cell (4). With this in mind, the progress in the nanomedicine field in the last decades, especially in the development of drug nanocarriers, has drawn attention, as these systems are able to enhance therapeutic efficacy by transporting drugs towards the specific intracellular target, thus reducing the toxic effects and the required drug treatment concentration (14, 15). Since 1995, the benefits of nanodrugs have been successfully incorporated into anticancer therapies, particularly in reducing the toxicity of traditional treatments (16, 17). Unfortunately, nanotechnology has not yet achieved its maximum drug delivery performance for CD treatment since nanocarriers loaded with high doses of antichagasic drugs or the high administration frequency of nanocarriers loaded with low-dose drugs seems to be essential for a sufficient trypanocidal effect (12, 18, 19). Some progress, otherwise, have been reached lately. In the case of pediatric patients, the incorporation of BNZ in self-emulsifying drug delivery systems represented a therapeutic advance in view of the low toxic liquid formulation can collaborate for a more comfortable oral administration and better intestinal absorption, presenting a similar antichagasic efficacy of free BNZ (20). In terms of CD diagnosis, the nanotechnology based on nano-porous particles was able to concentrate *T. cruzi* antigens in urine of chagasic HIV-coinfected patients, allowing the early diagnosis with sensitivity comparable to molecular biology techniques, as qPCR (21).

Therefore, this study was proposed to deliver BNZ using polymersomes self-assembling from poly (ethylene glycol)-block-poly (propylene sulfide) (PEG-b-PPS) and to evaluate the BNZ-loaded polymersomes (BNZ-PS) efficacy in a murine model of acute CD. Based on our previous studies, PEG-b-PPS polymersomes (PS) accumulate within DCs and macrophages (13, 22-25), the primary targets of *T. cruzi* during acute infection (26). Our in vitro studies confirmed the BNZ-PS activity against *T. cruzi* amastigotes and revealed the intracellular colocalization of BNZ-PS and bioluminescent *T. cruzi* parasites after a myoblast "in vitro" infection. The efficient delivery of BNZ by PS proved to be better in the CD murine model after only two BNZ-PS injections, reducing the blood and heart parasitemia at doses 666-fold and 66-fold lower than the required standard dose of free BNZ, respectively. Furthermore, typical signals of BNZ toxicity were not observed after BNZ-PS treatment.

To the best of our knowledge, this is the first time that such low doses of BNZ were effective in reducing the parasitemia of *T. cruzi*-infected mice. Our findings demonstrate that the efficient delivery of BNZ by PEG-b-PPS polymersomes enables the antichagasic effect of BNZ to be achieved at significantly lower concentrations whilst simultaneously avoiding the major BNZ treatment drawback—the systemic toxicity.

Results and Discussion

BNZ nanoparticles. Benznidazole (BNZ), a nitroimidazole with poor water solubility, has been widely used in clinic for the treatment of *T. cruzi*. However, therapeutic efficacy requires the administration of high doses of BNZ to patients on a daily basis, resulting in high risks of toxicity and side effects (27, 28). Our previous studies have demonstrated that nanocarriers composed of poly (ethylene glycol)-block-poly (propylene sulfide) (PEG-b-PPS) could achieve high loading efficiency for diverse small molecules, increase water solubility, and enhance intracellular delivery (29-32). The PEG-b-PPS nanocarriers are both noninflammatory and non-toxic in mice (25, 33) and nonhuman primates (23). The vesicular nanocarriers, i.e. polymersomes (PS), displayed a superior capacity to target antigen-presenting cells, such as dendritic cells (DCs), and macrophages, in spleen and liver (25, 32). To enhance the therapeutic efficacy and decrease off-target toxicity, the BNZ-loaded PS (BNZ-PS) were achieved by loading BNZ into PEG-b-PPS PS via the thin-film rehydration method (FIG. 1A). The loading of BNZ into PS does not change the vesicular structure as verified using cryogenic transmission electron microscopy (CryoTEM) (FIG. 1B). The size distribution of PS and BNZ-PS was determined using dynamic light scattering (DLS) (FIG. 1C). The hydrodynamic size of BNZ-PS was ~115 nm, which is comparable to the unloaded PS (Table 1). Zeta potential showed that the surface charge of BNZ-PS was slightly positive, but effectively neutral, in PBS solution (Table 1). The encapsulation efficiency (% EE) and loading efficiency (% LE) of BNZ-PS were ~31% and ~1% respectively, as characterized by using liquid chromatography-mass spectrometry (LC-MS) (Table 1, FIG. 5).

TABLE 1

Characterization of PS and BNZ-loaded PS in PBS solution (pH = 7.4).

| Name of samples | Average diameter (nm) | Polydispersity index (PDI) | Zeta potential (mV) | Encapsulation efficiency (%) | Loading efficiency (% w/w) |
|---|---|---|---|---|---|
| Polymersomes (PS) | 120 ± 6.2 | 0.06 ± 0.01 | −1.97 ± 0.46 | N/A | N/A |
| BNZ-loaded polymersomes (BNZ-PS) | 114.3 ± 4.1 | 0.11 ± 0.02 | 4.92 ± 1.93 | ~31 | ~1 |

Figure 2A:
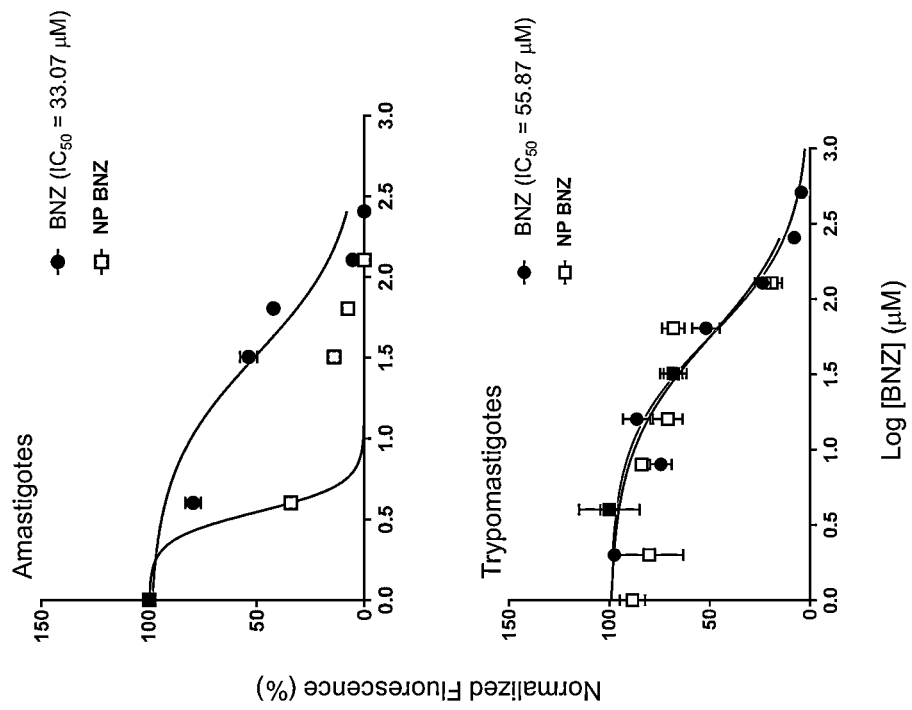
FIG. 2 Benznidazole polymersomes are more potent than free benznidazole against *T. cruzi* in vitro. (A) In vitro killing of purified trypomastigote and amastigote forms of *T. cruzi* by BNZ and BNZ-PS. Amastigotes and trypomastigotes were purified from infected H9C2 cell cultures and tested in a 24 h resazurin cell viability assay using increasing doses of BNZ or BNZ-PS. (B) PS are readily taken up by *T. cruzi*-infected H9C2 cells. H9C2 cells were infected with *T. cruzi* expressing Luc-mNeonGreen (green) for 24 h and Alexa630-labeled PS (yellow) were added and cultures incubated for an additional 24 h. Cells were imaged after staining with DAPI (blue) and Cell Mask Deep Red Dye (purple). (C) BNZ-PS are significantly more potent against intracellular *T. cruzi* than free BNZ. Cells were cultured and treated as in B, but with different concentrations of BNZ or BNZ-PS, and imaged after DAPI and Cell Mask staining. The key images for comparison are the left (*T. cruzi*) BNZ and BNZ-PS panels at each drug concentration.

IC50 for two strains of *T. cruzi*. The trypancidal effectiveness of BNZ-PS for Y and Tulauen strain was evaluated in vitro using the resarzurin assay (FIG. 2a). The half-inhibitory concentration (IC50) of free BNZ for Y and Tulauan strain trypomastigote was 55.87+−1.39 μM, 12.39+−2.41p M respectively. The IC50 of BNZ-PS for Y and Tulauan strain trypomastigote was 56.06+−12.218 μM, 6.28+−0.8 μM respectively.

Figure 2B:
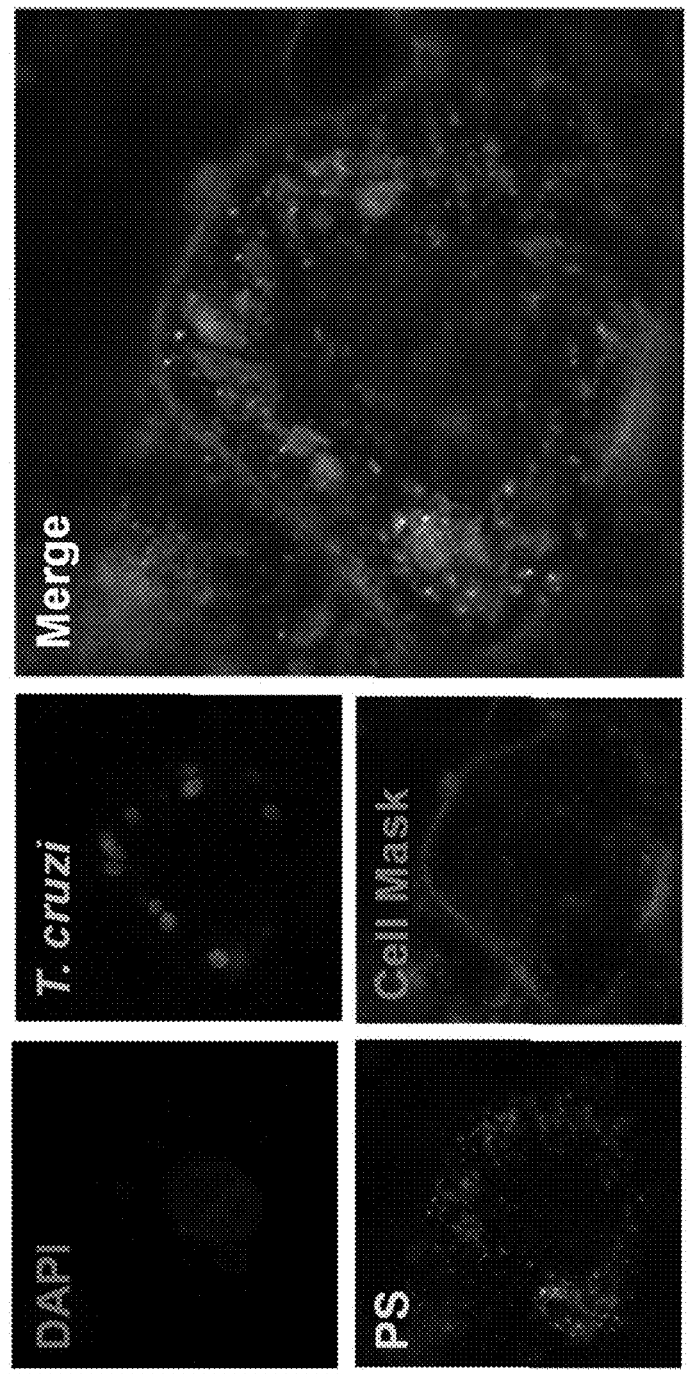
Figure 2C:
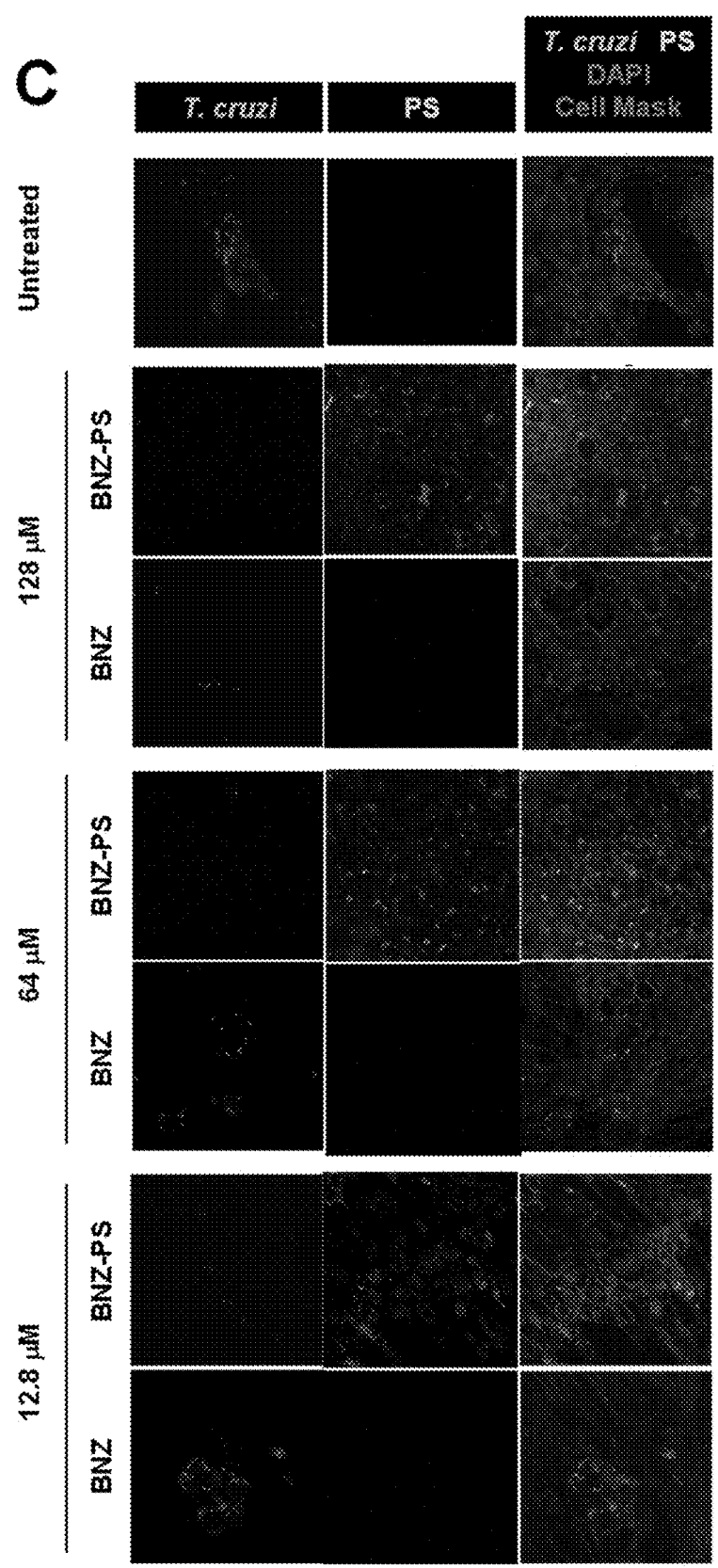

For Y strain, the amastigote killing effectiveness of BNZ-PS was evaluated in vitro using counting (FIG. 2b). The effectiveness for Tulauen strain amastigote killing was evaluated with bioluminescent quantification (FIG. 2c). BNZ-PS was significantly more efficient at killing amastigote both for Y and Tulauen strain, there was a 7-fold reduction in BNZ-PS relative to free BNZ. The IC50 of free BNZ for Y and Tulauan amastigote was 30.07+−8.17 μM, 12.47+−3.05 μM respectively. 4.404+−

Uptake and intracellular distribution of Benznidazole loaded polymersomes in *T. cruzi* infected H9C2 cells. Before investigating the effect of BNZ-PS, we first tested if the free PS could be efficiently taken up by the *T. cruzi* infected cells. For this purpose, the PS were conjugated with Alexa630, and then incubated with *T. cruzi* infected H9C2 cells for 4 h. As shown in FIG. 3a, the confocal imaging showed that free PS were confirmed to efficiently taken up by H9C2 cells after a 4 h incubation. We further validated the amastigote killing ability of Alexa630 conjugated PS loaded with BNZ at different BNZ concentration after incubated with *T. cruzi* infected H9C2 cells for 24 hours. As shown in FIG. 3b, BNZ loaded PS demonstrated stronger amastigote killing ability at same BNZ concentration.

The high incidence rate of side effects among *T. cruzi*-infected patients treated with BNZ (34,35) is a major issue for this drug therapy against Chagas disease. Although BNZ is better tolerated than Nfx, an average of 20% of the patients receiving the standard BNZ doses have to interrupt the treatment schedule due to the occurrence of severe side effects (34, 36). As Research and Development of new drugs to treat rare or neglected diseases require a high-risk investment for pharmaceutical industries, two alternative approaches have emerged that present a low failure rate and are less time-consuming for industries: the repurposing of drugs and the modification of effective old drugs to modulate their unsatisfactory properties (37). In the last decades, nanotechnology has led to a breakthrough in the development of drug delivery systems, especially regarding strategies of controlled drug release and targeted delivery. Therefore, not surprisingly, our results showed that nanoBNZ was successfully applied for the controlled release of BNZ into *T. cruzi*-infected cells. However, the most important contribution of our investigations for Chagas disease therapy is through the demonstration of how PEG-b-PPS vesicular nanocarriers, i.e. polymersomes, can optimize the BNZ delivery, enhancing the antichagasic efficacy, especially in the cardiac tissue of infected mice, minimizing the risk of BNZ toxic effects.

PEG-b-PPS is a physiologically inert copolymer used to assemble nanocarriers in a variety of shapes depending on the length of each polymer chain (22, 38). In this study, PEG-b-PPS was engineered to assemble vesicles loaded with BNZ, a hydrophobic drug, as the high hydrophobicity of the PPS polymer ensures stable BNZ incorporation. PPS hydrophobicity and PEG hydrophilicity are responsible for the creation of a highly stable macroamphiphile copolymer. However, when it comes to the application of nanomaterials against intracellular parasite infection, the disruption of nanocarrier stability in the cellular microenvironment is essential for effective intracellular drug delivery (39). Thus, although nanoparticles have to be designed to ensure high stability to protect the drug from degradation during long-term storage and to avoid accidental drug release in the patient before reaching the parasitized tissue, intracellular mechanisms must trigger the nanocarrier destabilization for consequent drug release (40-42).

Endocytic pathway is the primary mechanism for the cellular uptake of nanoparticles smaller than 500 nm (43), as PEG-b-PPS polymersomes. Oxidative enzymes inside the endolysosomal vacuoles, where PEG-b-PPS polymersomes are localized after endocytosis, promote the oxidation of sulfide moieties to sulfoxide in PPS block that modifies the hydrophilic-lipophilic balance of PEG-b-PPS copolymer. The oxidation process promotes a nanoarchitecture remodeling and consequent drug release during the initial stages of oxidation. The oxidation results in smaller amphiphiles blocks that may be inserted into the endosomal membrane, promoting the endosomal membrane permeabilization and consequent the escape of PEG-b-PPS vesicles to the cytosol, where the payload will also be released (30). The escape of nanocarriers toward the cytosol after endocytosis has been studied as a strategy to protect the pH-sensitive bioactive molecules from the acidic pH of endolysosomal vacuoles. For this purpose, nanocarriers are prepared from pH-sensitive polymers able to disrupt endosomal lipid bilayer membranes just in acidic pH, migrating to the cytosol for drug delivery (44).

Polymersomes and the *T. cruzi* parasite share this same route inside the cell. After invading phagocytic or non-phagocytic mammalian cells, *T. cruzi* trypomastigotes, are first restricted to the acidic endolysosomal compartments (i.e. parasitophorous vacuole), where they begin the differentiation process into amastigotes. The low pH enhances the activation of a porin-like protein, Tc-Tox, secreted by the intracellular *T. cruzi*. Tc-Tox lead to the formation of small pores to promote the fragmentation of endolysosomal vacuoles membrane, resulting in *T. cruzi* escape to the cytosol, a pH friendly environment, where the differentiation is completed (45, 46). Therefore, the colocalization of the PEG-b-PPS polymersomes and the parasite in the cytosol of host cells was the key feature for the choice of this intracellular delivery system for BNZ, and hence reason for the outstanding antiparasitic activity of nanoBNZ. These findings suggest that PEG-b-PPS polymersomes may be a suitable nanocarrier to deliver bioactive molecules against other pathogenic microorganisms residing freely in the cytosol. Some pathogenic bacteria and other protozoa have developed different strategies to escape from the harsh hydrolytic environment of the endolysosomal compartment to reside in the cell cytosol. Some of them, such as *Plasmodium* spp. (47), *Toxoplasma* spp. (48), *Rickettsia* spp. (49), and *Mycobacterium* spp. (50, 51) are responsible for causing severe and potentially disabling diseases, such as malaria, toxoplasmosis, rickettsiosis, and Hansen's disease and tuberculosis, respectively.

As endocytosis is the most common mechanism of nanoparticle cellular uptake, the colocalization of drug nanocarriers and intracellular parasites inside parasitophorous vacuoles are unquestionable. This is especially important for intracellular parasites such as *Leishmania* spp., a kinetoplastid parasite completely adapted to survive and replicate inside acidic endosomal vacuoles (52). The successful application of liposomal Amphotericin B against *Leishmania* spp. can be attributed to the release of Amphotericin B inside the parasitophorous vacuole, where *Leishmania* amastigotes reside. However, Amphotericin B hydrophobicity impairs its diffusion from the phagosome to the cytosol, hinder Amphotericin B reaching the parasites that eventually reside in the cytosol, outside the endosomal compartments (39). This explains the limited effectiveness of liposomal Amphotericin B in reducing the *T. cruzi* parasitic burden, despite the satisfactory Amphotericin B activity against extracellular *T. cruzi* developmental stages (18, 19, 53-55).

To complete its life cycle in the mammalian host, *T. cruzi* amastigotes differentiate once again into trypomastigotes, which are released into the bloodstream as a consequence of host cell rupture. Interrupting any point of the intracellular *T. cruzi* life cycle can result in the elimination of both amastigotes in the tissues and trypomastigotes in the bloodstream. Drugs that act predominantly against trypomastigotes tend to be less effective during the chronic stage of Chagas disease when the host immune response can control the trypomastigote burden whereas dormant amastigotes persist in tissues (56). Thus, although the low BNZ dose in nanoBNZ is not likely to be active against trypomastigotes in the blood mice, the efficient delivery into parasitized host cells caused a disruption of the parasite life cycle by killing the intracellular amastigotes, preventing the posterior transition to trypomastigotes and, consequently, reducing the blood parasitemia. Additionally, nanoBNZ was demonstrated to be more effective than oral BNZ in controlling heart inflammation. It is worth noting that although the autoimmune response may be related to the myocarditis in chronic Chagas disease, the reduction of parasite burden in the heart has to be considered in the mitigation of cardiac inflammation during the acute stage of Chagas disease (57). However, although oral BNZ significantly reduces the heart parasitemia, as well as the nanoBNZ treatment, the histological analysis revealed that just the nanoBNZ was able to control cardiac inflammation. Even a concentration of nanoBNZ that did not significantly reduce cardiac parasitemia was competent in reducing cardiac inflammation, suggesting that nanoBNZ has the additional benefit of ameliorating this symptom regardless of the presence of parasites in the heart. These findings justify further studies of nanoBNZ as a promising strategy against chronic Chagas disease.

Whilst in the acute phase of Chagas disease the ability of BNZ in reducing the trypomastigote number in the peripheral bloodstream is undeniable, the limited efficiency in reducing the persistent *T. cruzi* amastigote number in reservoir organs and symptoms of cardiomyopathy are the reasons for the questionable efficacy of traditional BNZ in the chronic stage (11, 58). Such phenomena can be understood by considering the pharmacokinetic properties of the traditional BNZ oral formulation: after intestinal absorption, the low permeation across the cell membrane (55) is responsible for maintaining a high BNZ plasma concentration, although over 40% of the drug is inactive by being bound to plasmatic proteins. The colocalization of trypomastigotes and BNZ in vascular compartments support the intense BNZ activity against blood trypomastigotes (18). As low doses of standard BNZ, such as those present in nanoBNZ, would not show trypanocidal activity (59), our findings indicate that nanoBNZ activity is a consequence of the improvement of permeation promoted by the PEG-b-PPS nanocarrier.

The BNZ sustained release must also be considered as an essential aspect of the nanoBNZ treatment. Sustained drug release for up to 12 days has already been reported for PEG-b-PPS nanocarriers in a previous study as a function of the PPS chain length, and it depends on drug partitioning from the hydrophobic PPS phase into water (29, 60). As BNZ is considered practically insoluble in water (9), its slow diffusion from PPS to the cellular microenvironment may have contributed to the successful antichagasic effect of only two nanoBNZ administrations during the 14 days of treatment. The low BNZ half-life in mice ($t_{1/2}$=2 h) supported by a high metabolic rate, including the first-pass metabolism after oral administration, and subsequent low bioavailability, is the reason for the administration of high BNZ daily doses (9). In humans, a greater half-life (t/2=12 h) (18) and a lower metabolic rate allow a lower dose in comparison to those given to mice, but still, daily doses are necessary to keep a high BNZ plasma concentration and consequently a high permeation cell rate to reach intracellular amastigotes (39). Although the daily administration increases the trypanocidal effect of BZN, it also enhances the systemic BNZ metabolism (18) resulting in toxic effects, the major drawback about BNZ treatment. As a prodrug, BNZ must be metabolized by *T. cruzi* type I nitroreductases, which are absent in humans, in order to become active. However, BNZ can also be metabolized by mammalian cells through type II nitroreductases, producing toxic metabolites for the host, such as reactive oxygen and nitrogen species (18). High BNZ dose regimens and the accumulation of BNZ after many days of treatment may be responsible for the severity of systemic toxic effects (61, 62). Thus, in terms of toxicity, our findings corroborate that low doses of BNZ and a reduced number of doses as well do not cause hepatotoxic effects and weight loss, which are common toxic signals from oral BNZ treatment in *T. cruzi* infected mice. Therefore, the nanoBNZ competence in promoting a sustained BNZ release in mice may represent a remarkable advantage over the traditional BNZ formulation, especially concerning the BNZ toxicity.

In conclusion, the efficiency of nanoBNZ in minimizing the heart inflammation, the cardiac amastigote burden, and the trypomastigote parasitemia, without causing the typical toxic signals, reinforces the idea that overcoming the BNZ pharmacokinetic issues to improve the cellular biodistribution in solid organs is critical for optimizing the antichagasic effect of low BNZ doses (11, 63). In a broader field, PEG-b-PPS polymersomes should be explored as a drug delivery system against other intracellular parasites since their multifaceted properties allow the encapsulation of hydrophobic and hydrophilic drugs simultaneously (22), as well as promoting the payload delivery into vacuoles and cytosol.

REFERENCES FOR EXAMPLE 1

1. Chagas C. Nova tripanozomiaze humana: estudos sobre a morfolojia e o ciclo evolutivo do Schizotrypanum cruzi n. gen., n. sp., ajente etiolojico de nova entidade morbida do homem. *Mem Inst Oswaldo Cruz.* 1909; 1:159-218.
2. Chagas C. Nova entidade morbida do homem: rezumo geral de estudos etiolojicos e clinicos. *Mem Inst Oswaldo Cruz.* 1911; 3:219-75.
3. Coura J R, and Vinas P A. Chagas disease: a new worldwide challenge. *Nature.* 2010; 465:S6-7.
4. Clayton J. Chagas disease 101. *Nature.* 2010; 465:S4-5.
5. Garza M, Feria Arroyo T P, Casillas E A, Sanchez-Cordero V, Rivaldi C L, and Sarkar S. Projected future distributions of vectors of *Trypanosoma cruzi* in North America under climate change scenarios. *PLoS Negl Trop Dis.* 2014; 8:e2818.
6. Liu Q, and Zhou X N. Preventing the transmission of American trypanosomiasis and its spread into non-endemic countries. *Infect Dis Poverty.* 2015; 4:60.
7. WHO. Chagas disease (American trypanosomiasis). World Health Organization Web Site. https://www.who.int/health-topics/chagas-disease#=tab_1. Accessed Jul. 22, 2020.
8. Bern C. Antitrypanosomal Therapy for Chronic Chagas' Disease. *N Engl J Med.* 2011; 364:2527-34.
9. Perin L, Moreira da Silva R, Fonseca K D, Cardoso J M, Mathias F A, Reis L E, Molina I, Correa-Oliveira R, Vieira P M, and Carneiro C M. Pharmacokinetics and Tissue Distribution of Benznidazole after Oral Administration in Mice. *Antimicrob Agents Chemother.* 2017; 61:e02410-16.
10. Andrade D V, Gollob K J, and Dutra W O. Acute chagas disease: new global challenges for an old neglected disease. *PLoS Negl Trop Dis.* 2014; 8:e3010.
11. Sales Junior P A, Molina I, Fonseca Murta S M, Sánchez-Montalvi A, Salvador F, Corrêa-Oliveira R, and Carneiro C M. Experimental and Clinical Treatment of Chagas Disease: A Review. *Am J Trop Med Hyg.* 2017; 97:1289-303.
12. Arrua E C, Seremeta K P, Bedogni G R, Okulik N B, and Salomon C J. Nanocarriers for effective delivery of benznidazole and nifurtimox in the treatment of chagas disease: A review. *Acta Trop.* 2019; 198:105080.
13. Field M C, Horn D, Fairlamb A H, Ferguson M A J, Gray D W, Read K D, De Rycker M, Torrie L S, Wyatt P G, Wyllie S, et al. Anti-trypanosomatid drug discovery: an ongoing challenge and a continuing need. *Nat Rev Microbiol.* 2017; 15:217-31.
14. Kreuter J. Nanoparticles—a historical perspective. *Int J Pharm.* 2007; 331:1-10.
15. Ventola C L. Progress in Nanomedicine: Approved and Investigational Nanodrugs. *P T* 2017; 42:742-55.
16. Barenholz Y. Doxil(R)—the first FDA-approved nanodrug: lessons learned. *J Control Release.* 2012; 160:117-34.
17. van der Meel R, Sulheim E, Shi Y, Kiessling F, Mulder W J M, and Lammers T. Smart cancer nanomedicine. *Nat Nanotechnol.* 2019; 14:1007-17.
18. Morilla M J, and Romero E L. Nanomedicines against Chagas disease: an update on therapeutics, prophylaxis and diagnosis. *Nanomedicine (Lond).* 2015; 10:465-81.
19. Quijia Quezada C, Azevedo C S, Chameau S, Santana J M, Chorilli M, Carneiro M B, and Bastos I M D. Advances in nanocarriers as drug delivery systems in Chagas disease. *Int J Nanomedicine.* 2019; 14:6407-24.
20. Mazzeti A L, Oliveira L T, Goncalves K R, Schaun G C, Mosqueira V C F, and Bahia M T. Benznidazole self-emulsifying delivery system: A novel alternative dosage form for Chagas disease treatment. *Eur J Pharm Sci.* 2020; 145:105234.
21. Castro-Sesquen Y E, Gilman R H, Mejia C, Clark D E, Choi J, Reimer-McAtee M J, Castro R, Valencia-Ayala E, Flores J, Bowman N, et al. Use of a Chagas Urine Nanoparticle Test (Chunap) to Correlate with Parasitemia Levels in *T. cruzi*/HIV Coinfected Patients. *PLoS Negl Trop Dis.* 2016; 10:e0004407.
22. Allen S, Osorio O, Liu Y G, and Scott E. Facile assembly and loading of theranostic polymersomes via multi-impingement flash nanoprecipitation. *J Control Release.* 2017; 262:91-103.
23. Allen S D, Liu Y-G, Bobbala S, Cai L, Hecker P I, Temel R, and Scott E A. Polymersomes scalably fabricated via flash nanoprecipitation are non-toxic in non-human primates and associate with leukocytes in the spleen and kidney following intravenous administration. *Nano Res.* 2018; 11:5689-703.
24. Bobbala S, Allen S D, and Scott E A. Flash nanoprecipitation permits versatile assembly and loading of polymeric bicontinuous cubic nanospheres. *Nanoscale.* 2018; 10:5078-88.
25. Yi S, Allen S D, Liu Y G, Ouyang B Z, Li X, Augsornworawat P, Thorp E B, and Scott E A. Tailoring Nanostructure Morphology for Enhanced Targeting of Dendritic Cells in Atherosclerosis. *ACS Nano.* 2016; 10:11290-303.
26. Gil-Jaramillo N, Motta F N, Favali C B, Bastos I M, and Santana J M. Dendritic Cells: A Double-Edged Sword in Immune Responses during Chagas Disease. *Front Microbiol.* 2016; 7:1076.
27. Castro J A, de Mecca M M, and Bartel L C. Toxic side effects of drugs used to treat Chagas' disease (American trypanosomiasis). *Hum Exp Toxicol.* 2006; 25:471-9.
28. Molina I, Gómez i Prat J, Salvador F, Treviño B, Sulleiro E, Serre N, Pou D, Roure S, Cabezos J, Valerio L, et al. Randomized Trial of Posaconazole and Benznidazole for Chronic Chagas' Disease. *N Engl J Med.* 2014; 370:1899-908.
29. Allen S D, Liu Y-G, Kim T, Bobbala S, Yi S, Zhang X, Choi J, and Scott E A. Celastrol-loaded PEG-b-PPS nanocarriers as an anti-inflammatory treatment for atherosclerosis. *Biomater Sci.* 2019; 7:657-68.
30. Scott E A, Stano A, Gillard M, Maio-Liu A C, Swartz M A, and Hubbell J A. Dendritic cell activation and T cell priming with adjuvant- and antigen-loaded oxidation-sensitive polymersomes. *Biomaterials.* 2012; 33:6211-9.

31. Vasdekis A E, Scott E A, O'Neil C P, Psaltis D, and Hubbell J A. Precision Intracellular Delivery Based on Optofluidic Polymersome Rupture. *ACS Nano.* 2012; 6:7850-7.
32. Yi S, Zhang X, Sangji M H, Liu Y, Allen S D, Xiao B, Bobbala S, Braverman C L, Cai L, Hecker P I, et al. Surface Engineered Polymersomes for Enhanced Modulation of Dendritic Cells During Cardiovascular Immunotherapy. *Adv Funct Mater.* 2019; 29:1904399.
33. Dowling D J, Scott E A, Scheid A, Bergelson I, Joshi S, Pietrasanta C, Brightman S, Sanchez-Schmitz G, Van Haren S D, Ninkovid J, et al. Toll-like receptor 8 agonist nanoparticles mimic immunomodulating effects of the live BCG vaccine and enhance neonatal innate and adaptive immune responses. *J Allergy Clin Immunol.* 2017; 140:1339-50.
34. Olivera M J, Cucunubi Z M, Valencia-Hemndez C A, Herazo R, Agreda-Rudenko D, Flórez C, Duque S, and Nicholls R S. Risk factors for treatment interruption and severe adverse effects to benznidazole in adult patients with Chagas disease. *PLOS ONE.* 2017; 12:e0185033.
35. Sperandio da Silva G M, Felix Mediano M F, Hasslocher-Moreno A M, Holanda M Td, Silvestre de Sousa A, Sangenis L H C, Brasil PEAAd, Mejia R A, Fux C P, Cubides J-C, et al. Benznidazole treatment safety: the Medecins Sans Frontières experience in a large cohort of Bolivian patients with Chagas' disease. *J Ant Chem.* 2017; 72:2596-601.
36. DNDi. Study shows dramatically shorter treatment for Chagas disease could be just as effective, and significantly safer. Drugs for Neglected Diseases Initiative Web Site. https://dndi.org/press-releases/2019/study-shows-dramatically-shorter-treatment-chagas-effective-and-safer/. Accessed Jul. 22, 2020.
37. Pushpakom S, Iorio F, Eyers P A, Escott K J, Hopper S, Wells A, Doig A, Guilliams T, Latimer J, McNamee C, et al. Drug repurposing: progress, challenges and recommendations. *Nat Rev Drug Discov.* 2019; 18:41-58.
38. Napoli A, Valentini M, Tirelli N, Müller M, and Hubbell J A. Oxidation-responsive polymeric vesicles. *Nat Mater.* 2004; 3:183-9.
39. Romero E L, and Morilla M J. Nanotechnological approaches against Chagas disease. *Adv Drug Deliv Rev.* 2010; 62:576-88.
40. Cooper D L, Conder C M, and Harirforoosh S. Nanoparticles in drug delivery: mechanism of action, formulation and clinical application towards reduction in drug-associated nephrotoxicity. *Expert Opin Drug Deliv.* 2014; 11:1661-80.
41. Ezrahi S, Aserin A, and Garti N. Basic principles of drug delivery systems—the case of paclitaxel. *Adv Colloid Interface Sci.* 2019; 263:95-130.
42. Ladaviere C, and Gref R. Toward an optimized treatment of intracellular bacterial infections: input of nanoparticulate drug delivery systems. *Nanomedicine.* 2015; 10:3033-55.
43. Zhao J, and Stenzel M H. Entry of nanoparticles into cells: The importance of nanoparticle properties. *Polym Chem.* 2018; 9:259-72.
44. Smith S A, Selby L I, Johnston A P R, and Such G K. The Endosomal Escape of Nanoparticles: Toward More Efficient Cellular Delivery. *Bioconjugate Chem.* 2019; 30:263-72.
45. Andrews N W, Abrams C K, Slatin S L, and Griffiths G. A *T. cruzi*-secreted protein immunologically related to the complement component C9: evidence for membrane pore-forming activity at low pH. *Cell.* 1990; 61:1277-87.
46. de Souza W, de Carvalho T M U, and Barrias E S. Review on *Trypanosoma cruzi*: host cell interaction. *Int J Cell Biol.* 2010; 2010.
47. Goldberg D E, and Zimmerberg J. Hardly Vacuous: The Parasitophorous Vacuolar Membrane of Malaria Parasites. *Trends Parasitol.* 2020; 36:138-46.
48. Leiriao P, Rodrigues C D, Albuquerque S S, and Mota M M. Survival of protozoan intracellular parasites in host cells. *EMBO Rep.* 2004; 5:1142-7.
49. Andrews N W, and Webster P. Phagolysosomal escape by intracellular pathogens. *Parasitol Today (Personal ed).* 1991; 7:335-40.
50. Ray K, Marteyn B, Sansonetti P J, and Tang C M. Life on the inside: the intracellular lifestyle of cytosolic bacteria. *Nat Rev Microbiol.* 2009; 7:333-40.
51. van der Wel N, Hava D, Houben D, Fluitsma D, van Zon M, Pierson J, Brenner M, and Peters P J. *M. tuberculosis* and *M. leprae* Translocate from the Phagolysosome to the Cytosol in Myeloid Cells. *Cell.* 2007; 129:1287-98.
52. Shaw C D, and Carter K C. Drug delivery: lessons to be learnt from *Leishmania* studies. *Nanomedicine.* 2014; 9:1531-44.
53. Cencig S, Coltel N, Truyens C, and Carlier Y. Parasitic Loads in Tissues of Mice Infected with *Trypanosoma cruzi* and Treated with AmBisome. *PLOS Negl Trop Dis.* 2011; 5:e1216.
54. Clemons K V, Sobel R A, Martinez M, Correa-Oliveira R, and Stevens D A. Lack of Efficacy of Liposomal Amphotericin B Against Acute and Chronic *Trypanosoma cruzi* Infection in Mice. *Am J Trop Med Hyg.* 2017; 97:1141-6.
55. Pund S, and Joshi A. In: Grumezescu A M ed. *Nano- and Microscale Drug Delivery Systems.* Elsevier; 2017:439-80.
56. Sinchez-Valdéz F J, Padilla A, Wang W, Orr D, and Tarleton R L. Spontaneous dormancy protects *Trypanosoma cruzi* during extended drug exposure. *eLife.* 2018; 7:e34039.
57. Bonney K M, Luthringer D J, Kim S A, Garg N J, and Engman D M. Pathology and Pathogenesis of Chagas Heart Disease. *Annu Rev Pathol.* 2019; 14:421-47.
58. Morillo C A, Marin-Neto J A, Avezum A, Sosa-Estani S, Rassi Jr A, Rosas F, Villena E, Quiroz R, Bonilla R, and Britto C. Randomized trial of benznidazole for chronic Chagas' cardiomyopathy. *N Engl J Med.* 2015; 373:1295-306.
59. Cevey A C, Mirkin G A, Penas F N, and Goren N B. Low-dose benznidazole treatment results in parasite clearance and attenuates heart inflammatory reaction in an experimental model of infection with a highly virulent *Trypanosoma cruzi* strain. *Int J Parasitol Drugs Drug Resist.* 2016; 6:12-22.
60. Velluto D, Demurtas D, and Hubbell J A. PEG-b-PPS Diblock Copolymer Aggregates for Hydrophobic Drug Solubilization and Release: Cyclosporin A as an Example. *Mol Pharmaceutics.* 2008; 5:632-42.
61. Pinazo M-J, Muñoz J, Posada E, López-Chejade P, Gllego M, Ayala E, del Cacho E, Soy D, and Gascon J. Tolerance of Benznidazole in Treatment of Chagas Disease in Adults. *Antimicrob Agents Chemother.* 2010; 54:4896.
62. Viotti R, Vigliano C, Lococo B, Alvarez M G, Petti M, Bertocchi G, and Armenti A. Side effects of benznidazole as treatment in chronic Chagas disease: fears and realities. *Expert Rev Anti Infect Ther.* 2009; 7:157-63.
63. Rial M S, Scalise M L, Arrna E C, Esteva M I, Salomon C J, and Fichera L E. Elucidating the impact of low doses of nano-formulated benznidazole in acute experimental Chagas disease. *PLOS Negl Trop Dis.* 2017; 11:e0006119.

Materials and Methods of Example 1

Synthesis of PEG-b-PPS Copolymers and Loading of Benznidazole (BNZ) into Polymersomes PS (PS).

Polymersomes were prepared by the controlled self-assembly of poly (ethylene glycol)-bl-poly (propylene sulfide) (PEG-b-PPS) block copolymers with the 25%-45% molecular weight of hydrophilic PEG fraction in the total block copolymer. PEG-b-PPS block copolymers were synthesized as previously described (1). Briefly, the anionic ring-opening polymerization of propylene sulfide initiated by PEG thioacetate and end-capped with PEG mesylate. The obtained block copolymers ($PEG_{17}$-$PPS_{60}$-$PEG_{17}$) were purified by precipitation in methanol, and then characterized through NMR and gel permeation chromatography (GPC) (ThermoFisher Scientific). The loading of benznidazole (BNZ) into polymersomes (PS) was performed through thin film rehydration method in PBS as described previously (1, 2). Briefly, 30 mg of the copolymer ($PEG_{17}$-$PPS_{60}$-$PEG_{17}$) with or without 1.5 mg of BNZ was dissolved in 150 µL Tetrahydrofuran (THF) within 1.8 mL clear glass vials (ThermoFisher Scientific) and placed under vacuum to remove the solvent. The resulting thin films were dehydrated in sterile PBS (1 mL) under shaking at 1500 rpm for 48 h. The BNZ-PS were purified to remove free BNZ by Zeba Spin Desalting Columns (7K MWCO, ThermoFisher Scientific).

Characterization of BNZ-PS

The liquid chromatography-mass spectrometry (LC-MS) analysis was performed on a Bruker AmaZon-X. Samples were chromatographed on a Hypersil BDS C18 column (2.4 mm particle size, 2.1×50 mm) (Thermo Fisher) at 40° C. The separation was achieved by a gradient of water with 0.1% formic acid (eluent A) and acetonitrile with 0.1% formic acid (eluent B) with a flow rate of 0.3 mL min-1. Detection was performed at 324 nm and the injection volume was 2 µL. The gradient starts at 40% B for 1 min, increases to 100% B in 4 min, holds at 100% B for 5 min, decreases to 90% B in 0.1 min, and holds at 90% B for 1.9 min. The standard calibration solution of BNZ was prepared in acetonitrile/water (95:5 v/v) ranging from 3.125 to 100 mg/mL. BNZ-PS samples were dissolved in acetonitrile/water (95:5 v/v) and then filtered through 0.2 mm membrane (ThermoFisher Scientific). The loading efficiency (% LE) of the BNZ-PS was determined by the percentage of the loaded weight of BNZ in the total weight of BNZ-PS. The encapsulation efficiency (% EE) of the BNZ-PS was calculated by the percentage of BNZ weight loaded into the PS in the initial BNZ weight added. The size distribution and zeta potential of PS and BNZ-PS (1 mg/mL) were characterized by Zetasizer Nano-ZS (Malvern Instruments, UK) using a 4 mW He—Ne 633 laser. The morphology of PS and BNZ-PS was determined by cryo transmission electron microscopy (CryoTEM) as described previously (3). In brief, 200 mesh Cu grids with a lacey carbon membrane (EMS Cat #LC200-CU-100) were glow-discharged in a Pelco easiGlow glow discharger (Ted Pella Inc., Redding, Calif., USA) using an atmosphere plasma generated at 15 mA for 15 seconds with a pressure of 0.24 mbar. PS and BNZ-PS samples (4 µL, 10 mg/mL in PBS) were pipetted onto the grid and blotted for 5 s with a blot offset of +0.5 mm, followed by immediate plunging into liquid ethane within a FEI Vitrobot Mark III plunge freezing instrument (Thermo Fisher Scientific, Waltham, Mass., USA). The plunge-frozen grids were kept vitreous at −180° C. in a Gatan Cryo Transfer Holder model 626.6 (Gatan Inc., Pleasanton, Calif., USA) while viewing in a JEOL JEM1230 LaB6 emission TEM (JEOL USA, Inc., Peabody, Mass.) at 100 keV. Image data were collected by a Gatan Orius SC1000 CCD camera Model 831 (Gatan Inc., Pleasanton, Calif., USA). The images were processed and analyzed using ImageJ. To investigate the storage stability, BNZ-PS suspension (30 mg/mL in PBS) was kept in sealed tubes and maintained at 4° C. At different time points (0, 1, 4, 8, 15, and 45 days), the released or unloaded BNZ was removed by using Zeba Spin Desalting Columns (7K MWCO, ThermoFisher Scientific). The percentage of loaded BNZ in PS at different time points (compared to day 0) was determined by LC-MS according to the above-mentioned protocols.

Cells, Cell Culture and Parasite Purification

The Y strain of *T. cruzi* was used for all experiments. Epimastigotes were cultured using standard methods and tissue culture amastigotes and trypomastigotes were produced by the addition of log-phase epimastigotes to cultured H9C2 rat myoblast cells, which contain small numbers of metacyclic trypomastigotes capable of initiating mammalian cell infection. After several days of culture in H9C2 cells, amastigotes and trypomastigotes were purified for use in IC50 determination experiments.

IC50 Determination

For the evaluation of anti-amastigote activity of *T. cruzi* Y strain, 50,000 H9C2 cells were seeded in chamber slides (Nunc Lab-Tek II, ThermoFisher Scientific). After 24 h, at 37° C. and 5% $CO_2$, H9C2 cells were infected with *T. cruzi* Y strain trypomastigotes at a 1:5 host-to-parasite cell ratio for additional 24 h and washed. Then the plate was incubated with different dilutions of BNZ and BNZ-PS. The medium was replaced every 24 h and the slide was fixed and stained with Giemsa solution (Richard-Allan Scientific Giema Stain, ThermoFisher Scientific) after 48 h. The number of amastigotes/100 H9C2 cells was calculated for each chamber.

For the evaluation of anti-amastigote activity of *T. cruzi* Tulahuen strain, 5000 H9C2 cells were seeded in a 96 well clear bottom tissue culture plate (Thermo Scientific). After 24 hours, the culture was infected with Luc-mNeonGreen Tulahuen strain trypomastigotes at a 1:5 host-to-parasite cell ratio for 24 h. Free trypomastigotes were washed off and infected cells were incubated with different dilutions of BNZ, BNZ-PS, and PS for 48 h. The medium was replaced every 24 h. At 48 h, 10 µL of 15 mg $mL^{-1}$ luciferin were added into each well, and the luciferase intensity was measured using a IVIS Spectrum (Caliper Life Science) and the ROI was analyzed with Softmas Pro. Exposure time varied from 5 s to 15 s depending on signal intensity.

Anti-Trypomastigote Activity

Resazurin method was used to evaluate in vitro anti-trypanosoma activity against Y trypomastigotes. $1 \times 10^7$ trypomastigotes $mL^{-1}$ were incubated in 96-well plates containing serial dilution of BNZ and BNZ-PS in RPMI 2640 medium with 5% FBS, penicillin (100 µL/mL), streptavidin (100 µL/mL) and L-glutamine (2 mM). For BNZ, the stock solution (1024 mM) was prepared in DMSO and made serial dilution to 1024 µM, 512 µM, 256 µM, 128 µM, 64 µM, 32 µM, 16 µM, 8 µM, 4 µM. For BNZ-PS, the stock solution (BNZ 1170 µM) was made serial dilution to 256 µM, 128 µM, 64 µM, 32 µM, 16 µM, 8 µM, 4 µM, 2 µM, 1 µM, 0.5 µM. After incubation for 24 h, at 37° C. and 5% $CO_2$, 10 µL of alamarBlue Cell Viability reagent (Invitrogen) were added in each well, then incubate at 37° C. for 4 h. The fluorescence was measure on a microplate reader (BMG Labtech) at 560/590 nm to evaluate trypomastigote viability. A log concentration vs response curve was generated and the BNZ IC50 was calculated in GraphPad Prism 7.0.

Nanoparticle Uptake

H9C2 cells were seeded in chamber slides (Nunc Lab-Tek II, Thermo Scientific) for 24 h followed by the infection with Luc-mNeonGreen Tulahuen strain trypomastigotes at 1:5 host to parasite cell ratio for 24 h. Free trypomastigotes were washed off and infected H9C2 cells were incubated with Alexa630 fluorescent labeled polymersomes for 24 h. Chamber slides were washed with PBS 5 times and stained with CellMask Deep Red Plasma Membrane Stain (Invitrogen) for 5 min and DAPI for 20 min. Leica confocal microscope were used to imaging the slide.

Mouse Infections

All animal protocols were reviewed and approved by the Institutional Animal Care And Use Committee of Cedars Sinai Medical Center (Protocol 7053). Female BALB/c mice (8-12 weeks of age) were purchased from Jackson Laboratories and on a 12-h dark-light cycle at 22±3° C. Mice had access to food and water ad libitum. $T.$ cruzi trypomastigotes used for infections were first passaged through female SCID mice (Jackson Labs). $2 \times 10^3$ in vitro derived trypomastigotes of Y strain (genotype TcII) in 0.2 ml PBS were first inoculated in SCID mice via i.p. injection. Peripheral blood parasitemia was determined by Brener methods. When SCID mice parasitemia reached to $1 \times 10^8$ parasites $ml^{-1}$, infected blood from SCID mice was harvested and adjusted to $2 \times 10^4$ blood derived trypomastigotes (BTs) $mL^{-1}$. Balb/c mice were infected with $2 \times 10^3$ BTs via i.p. injection. Parasitemia of Y strain-infected mice was determined every other day by trypomastigotes quantification in 3 µL of blood samples obtained from the saphenous vein.

BNZ and BNZ-PS Therapy

For drug treatments, BNZ-PS was prepared as mentioned above and BNZ (Sigma-Aldrich) was prepared from powder at 22 mg $mL^{-1}$ in 5% methylcellulose. After confirmation of the infection (seven dpi), 30 mice were randomized in to 6 equal groups as follow: 1) untreated control, 2) mice treated with 0.3 mg/mL of polymersome (PS) i.v., 3) mice treated with BNZ 100 mg/kg body weight for 14 days p.o., 4) mice treated with BNZ loaded-PS at a BNZ dose of 1.5 mg/kg body weight once every seven days for a total of two doses i.v., 5) mice treated with BNZ-PS at a BNZ dose of 0.15 mg/kg body weight once every seven days for a total of two doses i.v., 6) mice treated with BNZ-PS at a BNZ dose of 0.03 mg/kg body weight once every seven days for a total of two doses i.v. At 25 dpi, all infected animals were euthanized under deep anesthesia. Blood and organs were collected for further analysis.

Tissue Parasite Load

Organs and tissues were harvested then snap frozen on dry ice. DNA were extracted using QIAamp DNA Mini Kit (Qiagen) following the manufacturer's instruction. To make the standard for parasite burden quantification, 25 mg of skeletal muscle, liver, heart or 10 mg of spleen tissue of non-infected mouse were mixed with $1 \times 10^7$ $T.$ cruzi trypomastigotes. Total DNA was extracted, and the concentration was adjusted to 50 ng/µL. The standard curve was established from serial dilution of the sample range from $1 \times 10^7$ to $1 \times 10^{-1}$ parasite equivalence. Real-time PCR reactions were carried out using the QuantStudio 5 (ThermoFisher Scientific) machine. PCR reactions contained 50 ng of DNA, 0.5 µL of primers TCZ-F 5'-GCTCTTGCC-CACAMGGGTGC-3' (SEQ ID NO.: 1) and TCZ-R 5'-CCAAGCAGCGGATAGTTCAGG-3' (SEQ ID NO: 2), and 10 µL of EXPRESS SYBR GreenER™ qPCR Supermix (Invitrogen) in a final volume of 20 µL. Reactions were run in triplicate on as follow: 50° C. for 2 min and 40 cycles of 95° C. for 10 s, 55° C. for 15 s, 72° C. for 5 s. Mouse specific GAPDHf and GAPDHr were used as internal control.

Histopathological Studies

Heart was obtained from all groups, fixed in 10% buffered formalin for 15 h and embedded in paraffin. Five micrometer sections were stained with Hematoxylin & Eosin (H&E), Masson's Trichrome and Giemsa. The inflammatory index was derived by quantifying the total number of nuclei present in 10 randomly selected microscopic fields of each H&E stained sections. All slides were scanned using Aperio Scanscope AT scanner scanner, images were taken with ImageScope software and analyzed using ImageJ software Windows 64 by an investigator blinded to the groups.

Assessment of the Toxicity of BNZ and BNZ-PS In Vivo 25 healthy Balb/c mice was randomized into the following groups: 1) untreated control, 2) mice treated with 0.3 mg/mL of PS i.v., 3) mice treated with BNZ 100 mg/kg body weight for 14 days p.o., 4) mice treated with BNZ-PS at a BNZ dose of 1.5 mg/kg body weight once every 7 days for a total of two doses i.v., 5) mice treated with BNZ-PS at a BNZ dose of 0.15 mg/kg body weight once every 7 days for a total of two doses i.v. Mice weight was recorded during the treatment course. At day 15, mice were euthanized and serum and liver were collected. Serums (Sera) were sent out to central lab (IDEXX BioResearch) to measure alanine aminotransferase (ALT/SGPT), aspartate aminotransferase (AST/SGOT), bile acid, bilirubin, blood urea nitrogen (BUN), creatinine, gamma-glutamyltransferase (GGT).

Statistical Analysis

Numerical results of in vitro assays were expressed as the average±standard deviation (SD). Individual animals were used as the unit of analysis for in vivo and ex vivo experiments. Animal group size was determined empirically. One-way ANOVA and Tukey's multiple comparisons test were used in GraphPad Prism v.7 to evaluate groups difference. The level of significance is presented by $*p<0.05$.

REFERENCES FOR MATERIALS AND METHODS

1. Yi S, Zhang X, Sangji M H, Liu Y, Allen S D, Xiao B, et al. Surface Engineered Polymersomes for Enhanced Modulation of Dendritic Cells During Cardiovascular Immunotherapy. *Advanced Functional Materials.* 2019; 29(42):1904399.
2. Yi S, Allen S D, Liu Y-G, Ouyang B Z, Li X, Augsomworawat P, et al. Tailoring Nanostructure Morphology for Enhanced Targeting of Dendritic Cells in Atherosclerosis. *ACS Nano.* 2016; 10(12):11290-303.
3. Yi S, Karabin N B, Zhu J, Bobbala S, Lyu H, Li S, et al. An Injectable Hydrogel Platform for Sustained Delivery of Anti-inflammatory Nanocarriers and Induction of Regulatory T Cells in Atherosclerosis. *Frontiers in Bioengineering and Biotechnology.* 2020; 8:542.

We claim:

1. A pharmaceutical composition for treating Chagas disease comprising:
   a. a nanocarrier comprising:
      a poly(ethylene glycol)-block-poly(propylene sulfide) copolymer; and
      a therapeutic agent for treating Chagas disease selected from the group consisting of N-benzyl-2-(2-nitro-1H-imidazol-1-yl)acetamide (Benznidazole), N-(3-Methyl-1, 1-dioxido-4-thiomorpholinyl)-1-(5-nitro-2-furyl)methanimine (Nifurtimox), 1-Methyl-2-{[4-methyl sulfanyl)phenoxy]methyl}-5-nitro-1H-imidazole (Fexinidazole), 4-[4-[4-[4-[[(3R, 5R)-5-(2,4-difluorophenyl)tetrahydro-5-(1H-1,2,4-triazol-1-ylmethyl)-3-furanyl]methoxy]phenyl]-1-piperazinyl]phenyl]-2-[(1 S,2 S)-1-ethyl-2-hydroxypropyl]-2,4-dihydro-3H-1,2,4-triazol-3-one (Posaconazole), cysteine protease inhibitors, parasite proteasome inhibitors such as N-[4-fluoro-3-(6-pyridin-2-yl-[1,2,4]triazolo[1,5-a]pyrimidin-2-yl)phenyl]-2,4-dimethyl-1,3-oxazole-5-carboxamide; and
   b. one or more pharmaceutically acceptable excipients;
   wherein the therapeutic agent is formulated at a range of 0.025 mg/kg to 100 mg/kg.

2. The pharmaceutical composition of claim 1, wherein the therapeutic agent is N-benzyl-2-(2-nitro-1H-imidazol-1-yl)acetamide.

3. The pharmaceutical composition of claim 1, wherein the molar ratio of therapeutic agent: poly(ethylene glycol)-block-poly(propylene sulfide) copolymer is 0.001% to 50%.

4. The pharmaceutical composition of claim 1, wherein the poly(ethylene glycol)-block-poly(propylene sulfide) copolymer has a PEG weight fraction of 0.25 to 0.45.

5. The pharmaceutical composition of claim 1, wherein the poly(ethylene glycol)-block-poly(propylene sulfide) copolymer has a PEG weight fraction of 0.36.

6. The pharmaceutical composition of claim 1, wherein the poly(ethylene glycol)-block-poly(propylene sulfide) copolymer is a polymersome.

7. The pharmaceutical composition of claim 1, wherein the poly(ethylene glycol)-block-poly(propylene sulfide) copolymer is a hydrophobic core micelle.

8. The pharmaceutical composition of claim 1, wherein the therapeutic agent is formulated at a range of 0.025 mg/kg to 2 mg/kg.

9. The pharmaceutical composition of claim 1, wherein the pharmaceutically acceptable excipient is for intravenous administration.

10. A formulation for intravenous administration comprising the pharmaceutical composition of claim 9.

11. A polymersome for treating Chagas disease comprising:
   a poly(ethylene glycol)-block-poly(propylene sulfide) copolymer; and
   a therapeutic agent for treating Chagas disease selected from the group consisting of N-benzyl-2-(2-nitro-1H-imidazol-1-yl)acetamide (Benznidazole), N-(3-Methyl-1,1-dioxido-4-thiomorpholinyl)-1-(5-nitro-2-furyl)methanimine (Nifurtimox), 1-Methyl-2-{[4-methylsulfanyl)phenoxy]methyl}-5-nitro-1H-imidazole (Fexinidazole), 4-[4-[4-[4-[[(3R,5R)-5-(2,4-difluorophenyl)tetrahydro-5-(1H-1,2,4-triazol-1-ylmethyl)-3-furanyl]methoxy]phenyl]-1-piperazinyl]phenyl]-2-[(1S,2S)-1-ethyl-2-hydroxypropyl]-2,4-dihydro-3H-1,2,4-triazol-3-one (Posaconazole), cysteine protease inhibitors, parasite proteasome inhibitors such as N-[4-fluoro-3-(6-pyridin-2-yl-[1,2,4]triazolo[1,5-a]pyrimidin-2-yl)phenyl]-2,4-dimethyl-1,3-oxazole-5-carboxamide.

12. The polymersome of claim 11, wherein the therapeutic agent is N-benzyl-2-(2-nitro-1H-imidazol-1-yl)acetamide.

13. The polymersome of claim 11, wherein the molar ratio of therapeutic agent:
   poly(ethylene glycol)-block-poly(propylene sulfide) copolymer is 0.001% to 50%.

14. The polymersome of claim 11, wherein the poly(ethylene glycol)-block-poly(propylene sulfide) copolymer has a PEG weight fraction of 0.25 to 0.45.

15. The polymersome-of claim 11, wherein the poly(ethylene glycol)-block-poly(propylene sulfide) copolymer has a PEG weight fraction of 0.36.

* * * * *

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence -continued

```
<220> FEATURE:
<223> OTHER INFORMATION: synthetic

<400> SEQUENCE: 1
gctcttgccc acamgggtgc                                                    20

<210> SEQ ID NO 2
<211> LENGTH: 21
<212> TYPE: DNA
<213> ORGANISM: Artificial Sequence
<220> FEATURE:
<223> OTHER INFORMATION: synthetic

<400> SEQUENCE: 2
ccaagcagcg gatagttcag g                                                  21
```